(12) United States Patent
Yokoyama et al.

(10) Patent No.: US 9,818,949 B2
(45) Date of Patent: Nov. 14, 2017

(54) COMPOUND HAVING ACRIDAN RING STRUCTURE, AND ORGANIC ELECTROLUMINESCENT DEVICE

(71) Applicant: Hodogaya Chemical Co., Ltd., Tokyo (JP)

(72) Inventors: Norimasa Yokoyama, Tokyo (JP); Makoto Nagaoka, Tokyo (JP); Naoaki Kabasawa, Tokyo (JP); Eiji Takahashi, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/473,025

(22) Filed: Aug. 29, 2014

(65) Prior Publication Data

US 2015/0048351 A1    Feb. 19, 2015

Related U.S. Application Data

(63) Continuation of application No. 13/701,940, filed as application No. PCT/JP2011/003159 on Jun. 3, 2011, now Pat. No. 8,852,759.

(30) Foreign Application Priority Data

Jun. 7, 2010 (JP) .................................. 2010-129614

(51) Int. Cl.
*H01L 51/00* (2006.01)
*C07D 219/02* (2006.01)
(Continued)

(52) U.S. Cl.
CPC ........ *H01L 51/0052* (2013.01); *C07D 219/02* (2013.01); *C07D 401/10* (2013.01);
(Continued)

(58) Field of Classification Search
None
See application file for complete search history.

(56) References Cited

U.S. PATENT DOCUMENTS

2004/0219386 A1    11/2004  Thoms
2009/0066226 A1    3/2009   Sugita et al.
(Continued)

FOREIGN PATENT DOCUMENTS

CN    101671227 A    3/2010
CN    102272966 A    12/2011
(Continued)

OTHER PUBLICATIONS

International Search Report dated Jul. 12, 2011, issued for PCT/JP2011/003159.
(Continued)

*Primary Examiner* — J. L. Yang
(74) *Attorney, Agent, or Firm* — Locke Lord LLP; James E. Armstrong, IV; Nicholas J. DiCeglie, Jr.

(57) ABSTRACT

An organic compound with characteristics excelling in hole-injecting/transporting performance and having an electron blocking ability, a highly stable thin-film state, and excellent heat resistance is provided as material for an organic electroluminescent device of high efficiency and high durability, and the organic electroluminescent device of high efficiency and high durability is provided using this compound. The compound of a general formula (Chemical Formula 1) having a substituted acridan ring structure is used as a constituent material of at least one organic layer in the organic electroluminescent device that includes a pair of electrodes and one or more organic layers sandwiched between the pair of electrodes.

(Continued)

[Chemical Formula 1]

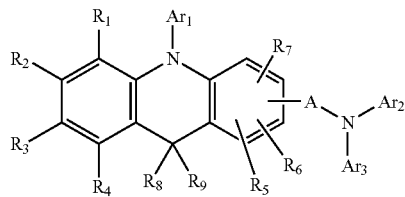

16 Claims, 4 Drawing Sheets

(51) Int. Cl.
| | |
|---|---|
| C07D 401/10 | (2006.01) |
| C07D 401/12 | (2006.01) |
| C07D 409/04 | (2006.01) |
| C07D 409/12 | (2006.01) |
| C07D 417/10 | (2006.01) |
| C07D 471/04 | (2006.01) |
| C09K 11/06 | (2006.01) |
| H05B 33/14 | (2006.01) |
| H01L 51/50 | (2006.01) |
| C07C 209/00 | (2006.01) |
| C07C 209/56 | (2006.01) |
| C07C 219/00 | (2006.01) |
| C07C 219/04 | (2006.01) |
| C07C 219/08 | (2006.01) |

(52) U.S. Cl.
CPC ......... *C07D 401/12* (2013.01); *C07D 409/04* (2013.01); *C07D 409/12* (2013.01); *C07D 417/10* (2013.01); *C07D 471/04* (2013.01); *C09K 11/06* (2013.01); *H01L 51/006* (2013.01); *H01L 51/0032* (2013.01); *H01L 51/0059* (2013.01); *H01L 51/0061* (2013.01); *H01L 51/0072* (2013.01); *H05B 33/14* (2013.01); *C07C 209/00* (2013.01); *C07C 209/56* (2013.01); *C07C 219/00* (2013.01); *C07C 219/04* (2013.01); *C07C 219/08* (2013.01); *C09K 2211/1007* (2013.01); *C09K 2211/1011* (2013.01); *C09K 2211/1014* (2013.01); *H01L 51/50* (2013.01); *H01L 51/5012* (2013.01); *H01L 51/5016* (2013.01); *H01L 51/5048* (2013.01); *H01L 51/5056* (2013.01); *H01L 51/5088* (2013.01); *H01L 51/5096* (2013.01)

(56) References Cited

U.S. PATENT DOCUMENTS

| | | |
|---|---|---|
| 2010/0066241 A1 | 3/2010 | Cho et al. |
| 2010/0096982 A1 | 4/2010 | Eum et al. |
| 2010/0219404 A1 | 9/2010 | Endo et al. |
| 2011/0266533 A1* | 11/2011 | Buesing ............... C07D 219/02 257/40 |
| 2012/0168730 A1 | 7/2012 | Kim et al. |

FOREIGN PATENT DOCUMENTS

| | | |
|---|---|---|
| EP | 2192633 A2 | 6/2010 |
| JP | 2009-021335 A | 1/2009 |
| JP | 2010-013444 A | 1/2010 |
| JP | 2010-059158 A | 3/2010 |
| WO | WO-2006/033563 A1 | 3/2006 |
| WO | WO-2006/033564 A1 | 3/2006 |
| WO | WO-2006/114966 A1 | 11/2006 |
| WO | WO-2007/110228 A1 | 10/2007 |
| WO | WO-2009/041635 A1 | 4/2009 |
| WO | WO-2010/083871 A1 * | 7/2010 ............ H01L 51/00 |
| WO | WO-2010/083871 A1 | 7/2010 |
| WO | WO-2010/147319 A2 | 12/2010 |

OTHER PUBLICATIONS

Supplementary European Search Report dated Oct. 21, 2013, issued for the European patent application No. 11792128.8.

Office Action dated Oct. 10, 2013, issued for the corresponding Chinese patent application.

Office Action dated Dec. 9, 2014, issued for the corresponding Taiwanese patent application (with its Japanese translation).

\* cited by examiner

[Fig.1]
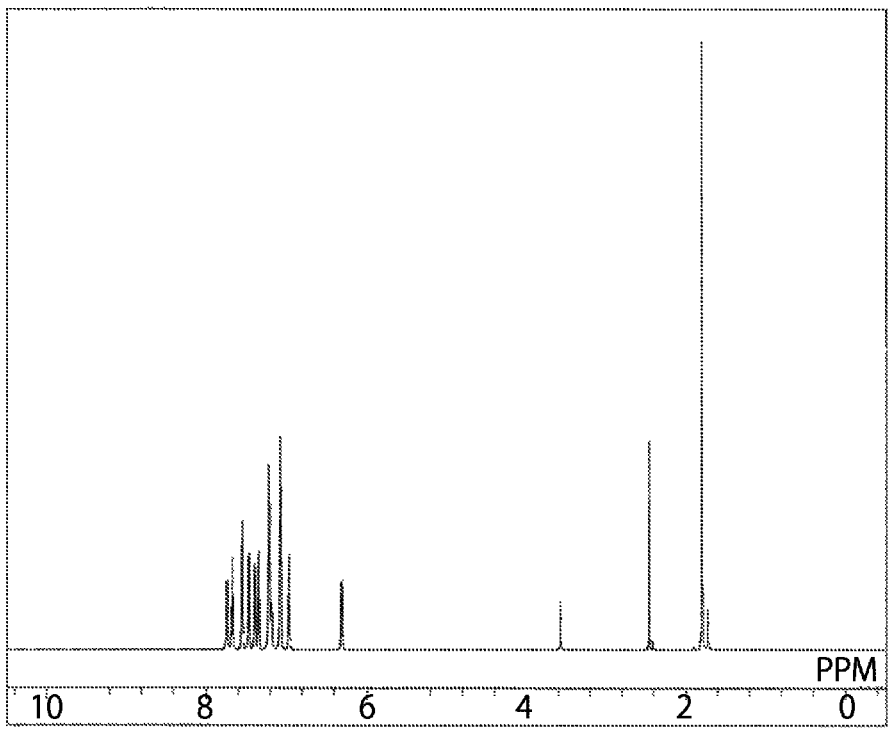
[Fig.2]
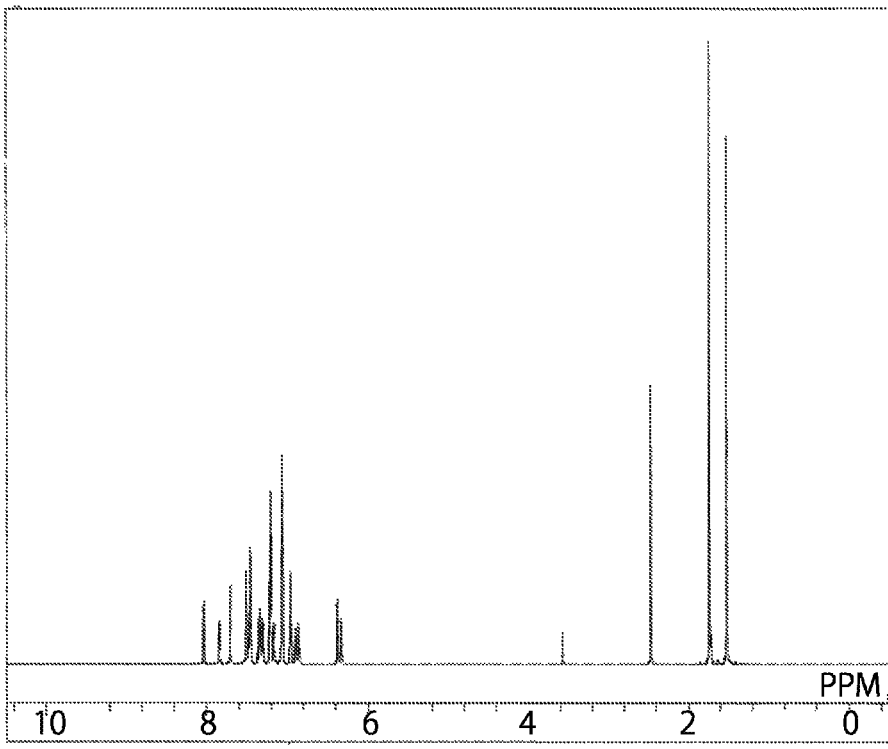

[Fig.3]
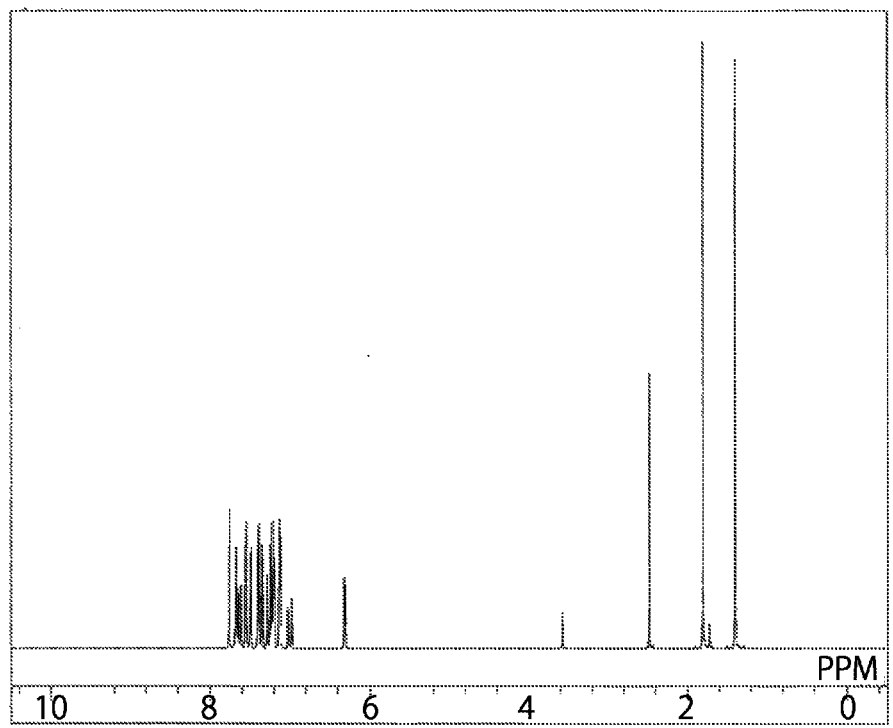
[Fig.4]
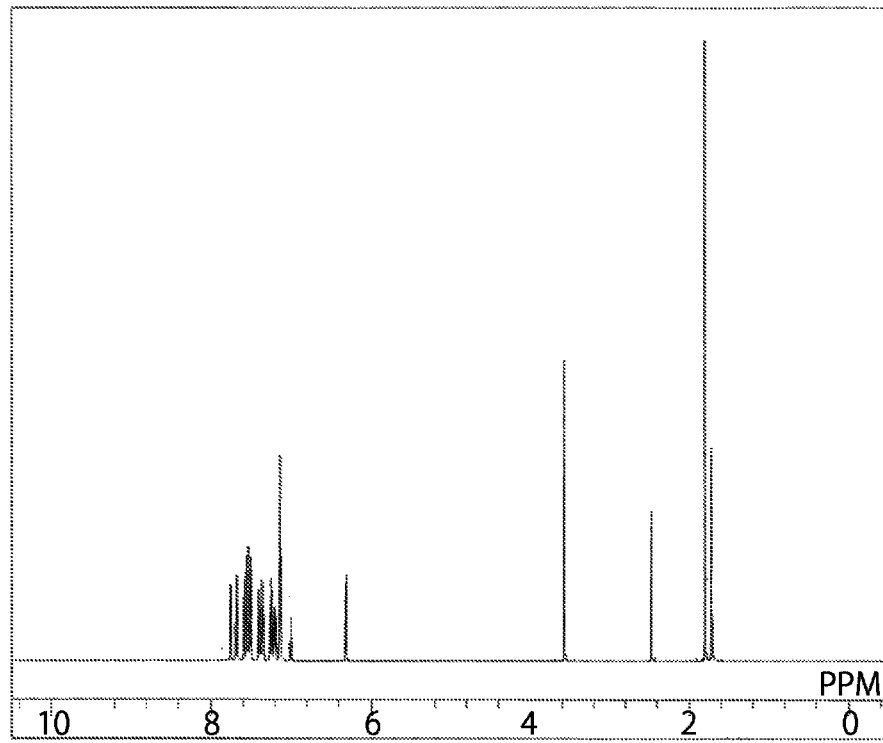

[Fig.5]
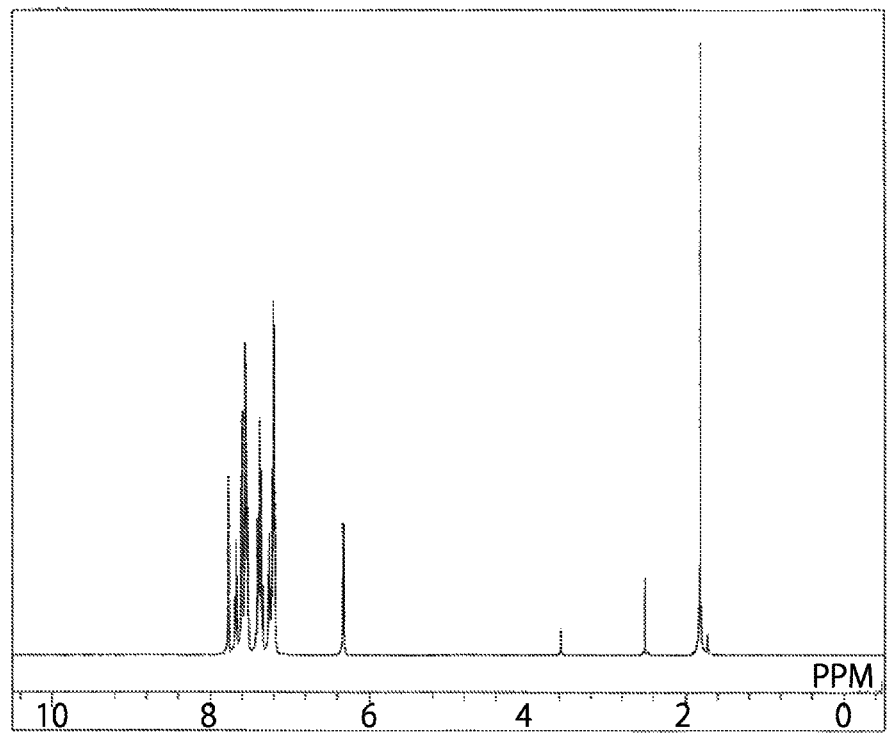
[Fig.6]
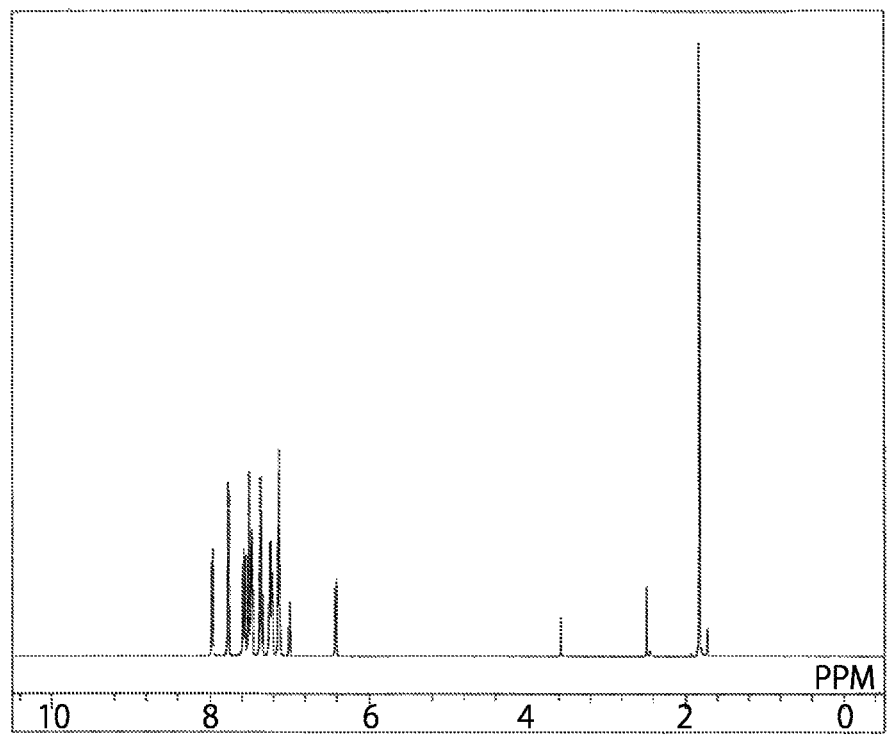

[Fig.7]
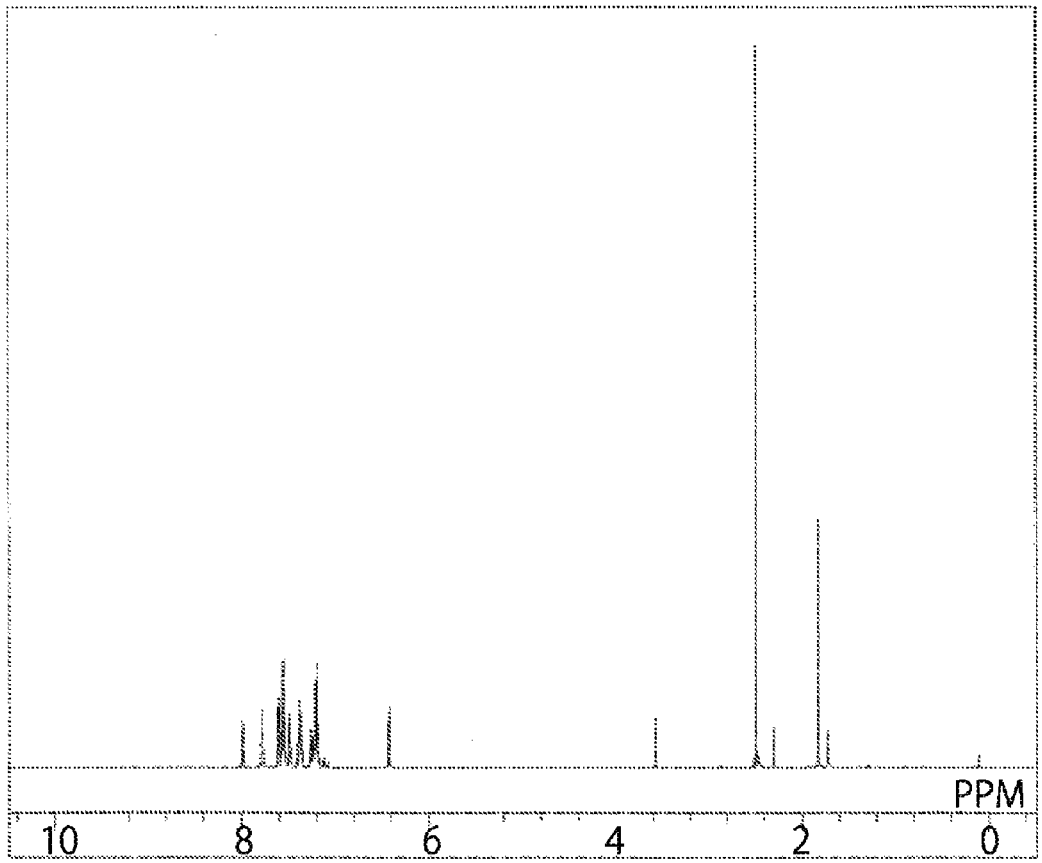
[Fig.8]
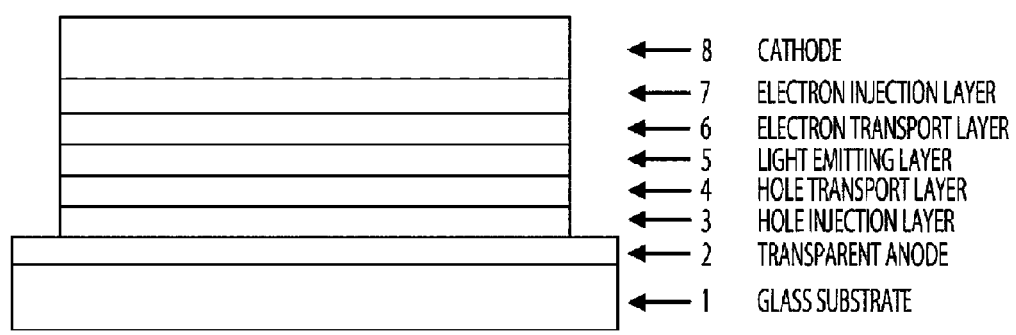
- 8 CATHODE
- 7 ELECTRON INJECTION LAYER
- 6 ELECTRON TRANSPORT LAYER
- 5 LIGHT EMITTING LAYER
- 4 HOLE TRANSPORT LAYER
- 3 HOLE INJECTION LAYER
- 2 TRANSPARENT ANODE
- 1 GLASS SUBSTRATE

COMPOUND HAVING ACRIDAN RING STRUCTURE, AND ORGANIC ELECTROLUMINESCENT DEVICE

CROSS REFERENCE TO RELATED APPLICATIONS

This application is a divisional application of U.S. application Ser. No. 13/701,940, filed Dec. 4, 2012, which application is a U.S. National stage application pursuant to 35 U.S.C. §371 of International Application No. PCT/JP2011/003159 filed Jun. 3, 2011, which application claims the benefit of priority under 35 U.S.C. §119 based on Japanese Patent Application No. 2010-129614 filed Jun. 7, 2010, the disclosures of which are expressly incorporated herein by reference in their entireties.

TECHNICAL FIELD

The present invention relates to compounds suitable for an organic electroluminescent device which is a preferred self-luminous device for various display devices, and relates to the organic electroluminescent device. Specifically, this invention relates to compounds having an acridan ring structure, and organic electroluminescent devices using the compounds.

BACKGROUND ART

The organic electroluminescent device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic electroluminescent device with organic materials. These researchers laminated an electron-transporting phosphor which is tris(8-hydroxyquinoline)aluminum (hereinafter referred to as Alq$_3$) and a hole-transporting aromatic amine compound, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic electroluminescent device. In order to realize high efficiency and durability, various roles are further subdivided to provide an electroluminescence device that includes an anode, a hole injection layer, a hole transport layer, a light emitting layer, an electron transport layer, an electron injection layer, and a cathode successively formed on a substrate (refer to Non-Patent Document 1, for example).

Further, there have been attempts to use triplet excitons for further improvements of luminous efficiency, and the use of phosphorescent materials has been examined (refer to Non-Patent Document 2, for example).

The light emitting layer can be also fabricated by doping a charge-transporting compound generally called a host material, with a phosphor or a phosphorescent material. As described in the foregoing lecture preprints, the selection of organic materials in an organic electroluminescent device greatly influences various device characteristics such as efficiency and durability.

In an organic electroluminescent device, charges injected from both electrodes recombine in a light emitting layer to cause emission. What is important here is how efficiently the hole and electron charges are transferred to the light emitting layer. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to a lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (hereinafter referred to as NPD) and various aromatic amine derivatives are known as the hole transport materials used for the organic electroluminescent device (refer to Patent Documents 1 and 2, for example). Although NPD has desirable hole transportability, it has a low glass transition point (Tg) of 96° C. which is an index of heat resistance and therefore causes the degradation of device characteristics by crystallization under a high-temperature condition (refer to Non-Patent Document 3, for example). The aromatic amine derivatives described in the Patent Documents 1 and 2 include a compound known to have an excellent hole mobility of 10$^{-3}$ cm$^2$/Vs or higher. However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency.

Arylamine compounds of the following formulae having a substituted acridan structure (for example, Compounds A and B) are proposed as compounds improved in the characteristics such as heat resistance, hole injectability and electron blocking performance (refer to Patent Documents 3 and 4, for example).

[Chemical Formula 1]

(Compound A)

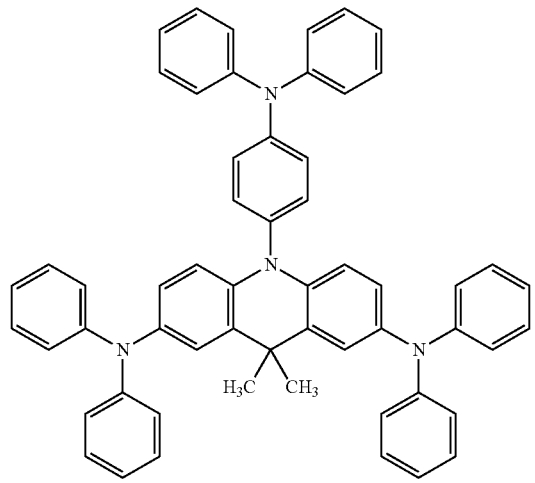

[Chemical Formula 2]

(Compound B)

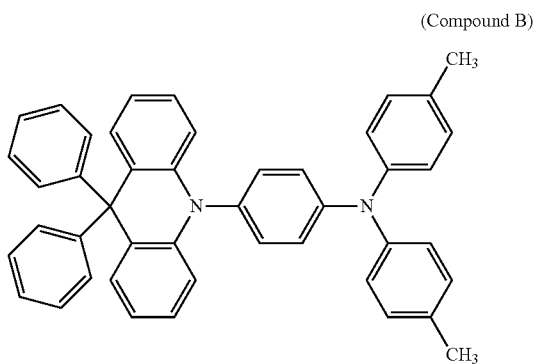

However, while the devices using these compounds for the hole injection layer or the hole transport layer have been improved in heat resistance, luminous efficiency and the like, the improvements are still insufficient. Further, it cannot be said to have a sufficiently low driving voltage and sufficient current efficiency, and there is a problem also in amorphousness. Further improvements of a low driving voltage and luminous efficiency while increasing amorphousness are therefore needed.

CITATION LIST

Patent Documents

Patent Document 1: JP-A-8-48656
Patent Document 2: Japanese Patent No. 3194657
Patent Document 3: WO2006/033563
Patent Document 4: WO2007/110228

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Organic EL Symposium, the 3rd Regular presentation Preprints, pp. 13 to 14 (2006)
Non-Patent Document 4: J. Org. Chem., 60, 7508 (1995)
Non-Patent Document 5: Chem. Rev., 95, 2457 (1995)
Non-Patent Document 6: Angew. Chem. Int. Ed., 42, 5400 (2003)

SUMMARY OF THE INVENTION

Problems to be Solved by the Invention

An object of the present invention is to provide an organic compound with characteristics excelling in hole-injecting/transporting performance and having electron blocking ability, high stability in a thin-film state and excellent heat resistance, the organic compound being provided as material for an organic electroluminescent device having high efficiency and high durability. This invention also provides the organic electroluminescent device of high efficiency and high durability using this compound.

Physical properties of the organic compound to be provided by the present invention include (1) good hole injection characteristics, (2) large hole mobility, (3) excellent electron blocking ability, (4) stability in the thin-film state, and (5) excellent heat resistance. Physical properties of the organic electroluminescent device to be provided by the present invention include (1) high luminous efficiency and high power efficiency, (2) low turn on voltage, and (3) low actual driving voltage.

In order to achieve the above objects, the present inventors designed compounds having an acridan ring structure in anticipation of the high hole-injecting/transporting ability of an aromatic tertiary amine structure, the electron blocking performance of the acridan ring structure, and the effect of heat resistance and thin-film stability of these partial structures. The present inventors produced various test organic electroluminescent devices using the compounds chemically synthesized to have the acridan ring structure, and the present invention was completed after thorough evaluations of the device characteristics.

Specifically, the present invention is a compound of the following general formula (1) having a substituted acridan ring structure.

[Chemical Formula 3]

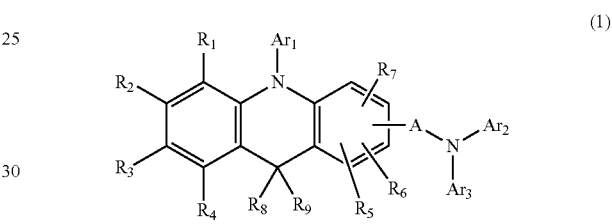

(1)

In the formula, A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics. Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is a compound of the following general formula (2) having a substituted acridan ring structure.

[Chemical Formula 4]

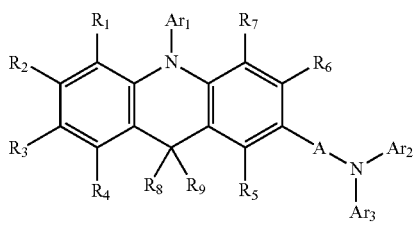

(2)

In the formula, A represents a divalent group of substituted or unsubstituted aromatic hydrocarbon, a divalent group of a substituted or unsubstituted aromatic heterocyclic ring, or a divalent group of substituted or unsubstituted condensed polycyclic aromatics. Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is a compound of the following general formula (3) having a substituted acridan ring structure.

[Chemical Formula 5]

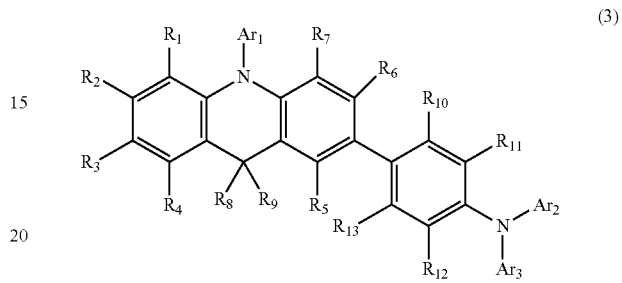

(3)

In the formula, Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7 and R10 to R13 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R2 and R3, R3 and R4, R6 and R7, R10 and R11, and R12 and R13 may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is a compound of the following general formula (4) having a substituted acridan ring structure.

[Chemical Formula 6]

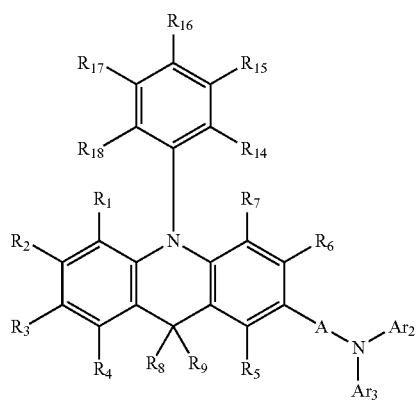

(4)

In the formula, A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics. Ar2 and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7 and R14 to R18 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R2 and R3, R3 and R4, R6 and R7, R14 and R15, R15 and R16, R16 and R17, and R17 and R18 may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is an organic electroluminescent device that includes a pair of electrodes and one or more organic layers sandwiched between the pair of electrodes, wherein the compound of the general formula (1), (2), (3), or (4) having a substituted acridan ring structure is used as a constituent material of at least one organic layer.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by R1 to R18 in general formulae (1) to (4), can be methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by R1 to R18 in general formulae (1) to (4) can be a deuterium atom; trifluoromethyl; cyano; nitro; halogen atoms such as a fluorine atom, a chlorine atom, a bromine atom, and an iodine atom; linear or branched alkoxys of 1 to 6 carbon atoms such as methoxy, ethoxy, and propyloxy; alkenyls such as allyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may be further substituted with other substituents. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by R1 to R18 in general formulae (1) to (4) can be methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms that has a substituent" or the "cycloalkyloxy of 5 to 10 carbon atoms that has a substituent" represented by R1 to R18 in general formulae (1) to (4) can be a deuterium atom; trifluoromethyl; cyano; nitro; halogen atoms such as a fluorine atom, a chlorine atom, a bromine atom, and an iodine atom; linear or branched alkoxys of 1 to 6 carbon atoms such as methoxy, ethoxy, and propyloxy; alkenyls such as allyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may be further substituted with other substituents. These substituents may bind to each other via a single bond, substituted or unsubstituted methylene, an oxygen atom, or a sulfur atom to form a ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by R1 to R18 in general formulae (1) to (4) can be phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These groups may bind to each other via a single bond, substituted or unsubstituted methylene, an oxygen atom, or a sulfur atom to form a ring.

Specific examples of the "substituent" in the "substituted aromatic hydrocarbon group", the "substituted aromatic heterocyclic group", or the "substituted condensed polycyclic aromatic group" represented by R1 to R18 in general formulae (1) to (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by R1 to R18 in general formulae (1) to (4) can be phenoxy, tolyloxy, biphenylyloxy, terphenylyloxy, naphthyloxy, anthryloxy, phenanthryloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

Specific examples of the "substituent" in the "substituted aryloxy" represented by R1 to R18 in general formulae (1) to (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as dialkylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted. These substituents may bind to each other via a single bond, substituted or unsubstituted methylene, an oxygen atom, or a sulfur atom to form a ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by Ar1 to Ar3 in general formulae (1) to (4) can be phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These groups may directly bind to each other via a single bond or via substituted or unsubstituted methylene to form a ring.

It is preferable that the "aromatic heterocyclic group" in the "substituted or unsubstituted aromatic heterocyclic group" represented by Ar2 to Ar3 in general formulae (1) to (4) is a sulfur-containing aromatic heterocyclic group such as thienyl, benzothienyl, benzothiazolyl, or dibenzothienyl.

Specific examples of the "substituent" in the "substituted aromatic hydrocarbon group", the "substituted aromatic heterocyclic group", or the "substituted condensed polycyclic aromatic group" represented by Ar1 to Ar3 in general formulae (1) to (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted. These substituents may bind to each other or bind to the "substituted aromatic hydrocarbon group", the "substituted aromatic heterocyclic group", or the "substituted condensed polycyclic aromatic group" represented by Ar1 to Ar3, via a single bond, substituted or unsubstituted methylene, an oxygen atom, or a sulfur atom to form a ring.

Specific examples of the "divalent group of an aromatic hydrocarbon", the "divalent group of an aromatic heterocyclic ring", or the "divalent group of condensed polycyclic aromatics" in the "divalent group of a substituted or unsubstituted aromatic hydrocarbon", the "divalent group of a substituted or unsubstituted aromatic heterocyclic ring", or the "divalent group of substituted Or unsubstituted condensed polycyclic aromatics" represented by A in general formulae (1), (2), and (4) can be phenylene, biphenylene, terphenylene, tetrakisphenylene, naphthylene, anthrylene, phenanthrylene, fluorenylene, phenanthrolylene, indenylene, pyrenylene, perylenylene, fluoranthenylene, triphenylenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, acridinylene, thienylene, benzothienylene, benzothiazolylene, and dibenzothienylene.

It is preferable that the "divalent group of an aromatic heterocyclic ring" in the "divalent group of a substituted or unsubstituted aromatic heterocyclic ring" represented by A in general formulae (1), (2), and (4) is a divalent group of a sulfur-containing aromatic heterocyclic ring such as thienylene, benzothienylene, benzothiazolylene, or dibenzothienylene.

Specific examples of the "substituent" in the "divalent group of a substituted aromatic hydrocarbon", the "divalent group of a substituted aromatic heterocyclic ring", or the "divalent group of substituted condensed polycyclic aromatics" represented by A in general formulae (1), (2), and (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; and acyls such as acetyl and benzoyl. These substituents may be further substituted. These substituents may bind to each other via a single bond, substituted or unsubstituted methylene, an oxygen atom, or a sulfur atom to form a ring.

Among the compounds of the general formula (4) having an acridan ring structure, the compounds of the following general formula (4'), (4''), (4'''), or (4'''') having an acridan ring structure are preferably used for an organic EL device.

[Chemical Formula 5]

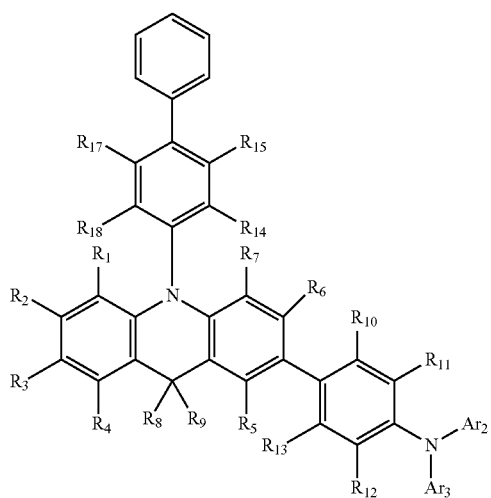

(4')

In the formula, Ar2 and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7, R10 to R13, R14, R15, R17, and R18 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R2 and R3, R3 and R4, R6 and R7, R10 and R11, R12 and R13, R14 and R15, and R17 and R18 may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

[Chemical Formula 6]

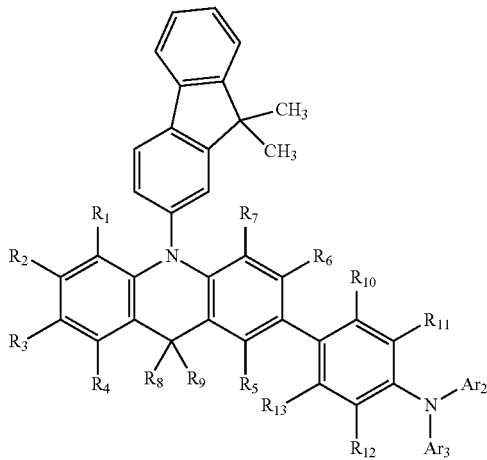

(4″)

In the formula, Ar2 and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1 to R7, and R10 to R13 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl, of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R2 and R3, R3 and R4, R6 and R7, R10 and R11, and R12 and R13 may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

[Chemical Formula 7]

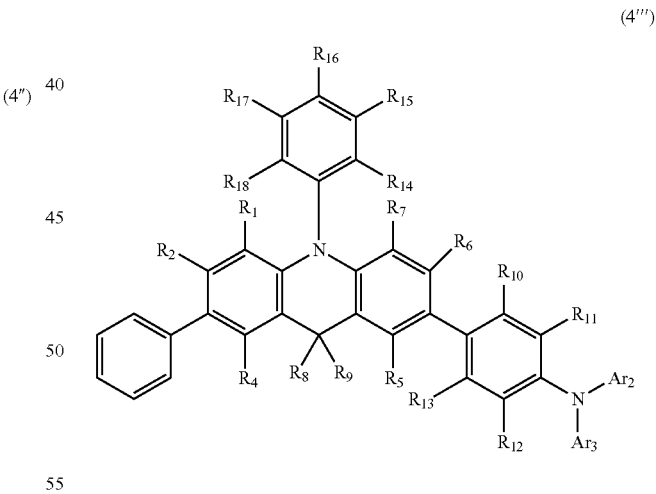

(4‴)

In the formula, Ar2 and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1, R2, R4 to R7, R10 to R13, and R14 to R18 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R6 and R7, R10 and R11, R12 and R13, R14 and R15, R15 and R16, R16 and R17, and R17 and R18 may bind to each other via a single bond, substituted or unsubstituted methylene, an oxygen atom, or a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a, sulfur atom to form a ring.

[Chemical Formula 8]

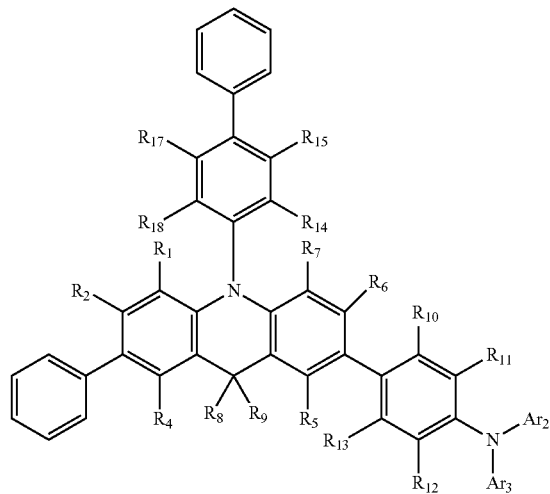

(4'''')

In the formula, Ar2 and Ar3 may be the same or different, and represent a substituted or unsubstituted aromatic hydrocarbon group, a substituted or unsubstituted aromatic heterocyclic group, or a substituted or unsubstituted condensed polycyclic aromatic group. Ar2 and Ar3 may directly bind to each other via a single bond or via substituted or unsubstituted methylene, an oxygen atom, or a sulfur atom to form a ring, and substituents of Ar2 and Ar3 may bind to each other via a single bond, substituted or unsubstituted methylene, an oxygen atom, or a sulfur atom to form a ring. R1, R2, R4 to R7, R10 to R13, R14, R15, R17, and R18 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, wherein R1 and R2, R6 and R7, R10 and R11, R12 and R13, R14 and R15, and R17 and R18 may bind each other via a single bond, substituted or unsubstituted methylene, an oxygen atom, or, a sulfur atom to form a ring. R8 and R9 may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group; a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

The compounds of general formulae (1) to (4) having an acridan ring structure of the present invention are novel compounds and have superior electron blocking ability, superior amorphousness and a more stable thin-film state compared to conventional hole transport materials.

The compounds of general formulae (1) to (4) having an acridan ring structure of the present invention can be used as a constituent material of the hole injection layer and/or hole transport layer of an organic electroluminescent device (hereinafter referred to as an organic EL device). With the use of material having higher hole injectability, higher mobility, higher electron blocking performance and higher stability to electrons than conventional materials, excitons generated in a light emitting layer can be confined, and the probability of hole-electron recombination can be improved. This improves luminous efficiency, lowers driving voltage and thus improves the durability of the organic EL device.

The compounds of general formulae (1) to (4) having an acridan ring structure of the present invention can also be used as a constituent material of the electron blocking layer of an organic EL device. With the use of material having an excellent electron blocking ability and having superior hole transportability and higher stability in a thin-film state than conventional materials, driving voltage is lowered and current resistance is improved while maintaining high luminous efficiency. As a result, the maximum emission luminance of the organic EL device is improved.

The compounds of general formulae (1) to (4) having an acridan ring structure of the present invention can also be used as a constituent material of the light emitting layer of the organic EL device. The material of the present invention having superior hole transportability and a wider band gap than conventional materials is used as the host material of the light emitting layer in order to form the light emitting layer by carrying a fluorescent material or phosphorescent material called a dopant. In this way, the organic EL device with a low driving voltage and improved luminous efficiency can be achieved.

The high efficiency and high durability of the organic EL device in the present invention can be achieved because of the use of the compound having an acridan ring structure, which has greater hole mobility, superior electron blocking ability and superior amorphousness than conventional hole transport materials as well as a stable thin-film state.

Effects of the Invention

The compound having an acridan ring structure of the present invention is useful as the constituent material of the hole injection layer, hole transport layer, electron blocking layer, or light emitting layer of the organic EL device. The compound has an excellent electron blocking ability and satisfactory amorphousness, and excels in heat resistance as well as a stable thin-film state. The organic EL device of the present invention has high luminous efficiency and high power efficiency, and the actual driving voltage of the device can thereby be lowered.

BRIEF DESCRIPTION OF THE DRAWINGS

FIG. 1 is a 1H-NMR chart of the compound of Example 1 of the present invention (Compound 11).

FIG. 2 is a 1H-NMR chart of the compound of Example 2 of the present invention (Compound 19).

FIG. 3 is a 1H-NMR chart of the compound of Example 3 of the present invention (Compound 27).

FIG. 4 is a 1H-NMR chart of the compound of Example 4 of the present invention (Compound 12).

FIG. 5 is a 1H-NMR chart of the compound of Example 5 of the present invention (Compound 13).

FIG. 6 is a 1H-NMR chart of the compound of Example 6 of the present invention (Compound 24).

FIG. 7 is a 1H-NMR chart of the compound of Example 7 of the present invention (Compound 23).

FIG. 8 is a diagram illustrating the configuration of the EL devices of Examples 10 and 11 and Comparative Example 1.

MODE FOR CARRYING OUT THE INVENTION

The compounds having an acridan ring structure of the present invention are novel compounds, and may be synthesized, for example, as follows. First, 2-bromo-10-arylacridan is synthesized by bromination of acridan substituted with an aryl group at the corresponding tenth position, using bromine, N-bromosuccinimide, or the like (refer to Patent Document 3, for example). Boronic acid or borate synthesized by the reaction of the resulting bromo compound with compounds such as pinacolborane and bis(pinacolato)diboron (refer to Non-Patent Document 4, for example) can then be reacted with aryl halides substituted with various diarylamino groups in a cross-coupling reaction such as Suzuki coupling (refer to Non-Patent Document 5, for example) to synthesize the compounds having an acridan ring structure.

The compounds having an acridan ring structure of the present invention may be synthesized also by using the following method. First, acridan substituted with an arylamino group at the corresponding second position can be reacted with various aryl halides in a cross-coupling reaction such as Ullmann coupling (refer to Non-Patent Document 6, for example), and the compounds having an acridan ring structure can then be synthesized.

The following presents specific examples of preferred compounds among the compounds of general formula (1) having an acridan ring structure. The present invention, however, is not restricted to these compounds.

[Chemical Formula 7]

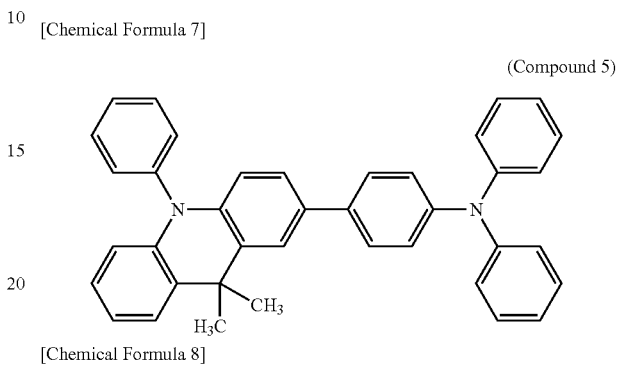

[Chemical Formula 8]

[Chemical Formula 9]

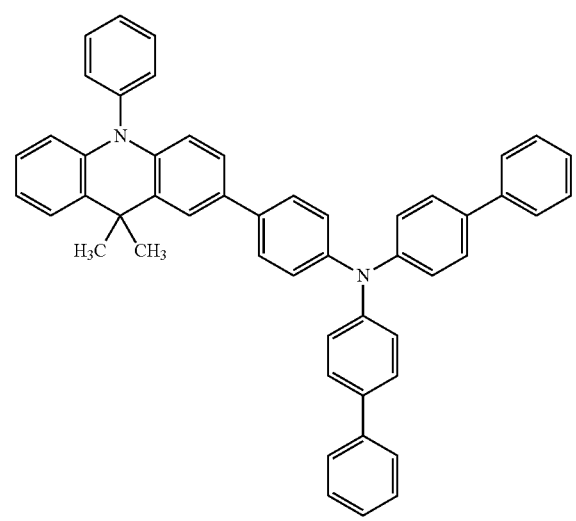

-continued
[Chemical Formula 10] (Compound 8)
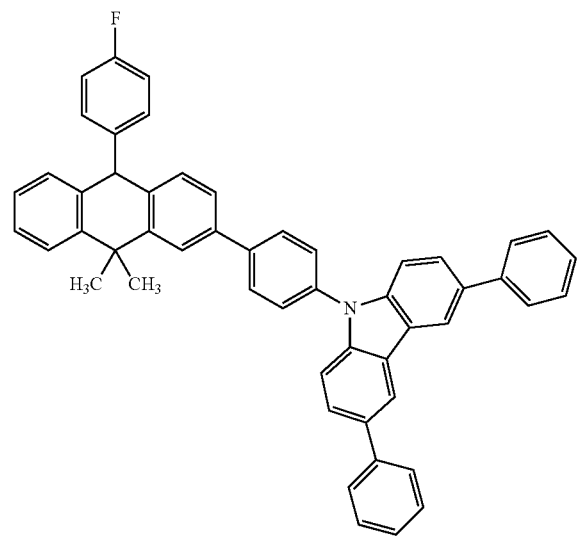
[Chemical Formula 11] (Compound 9)
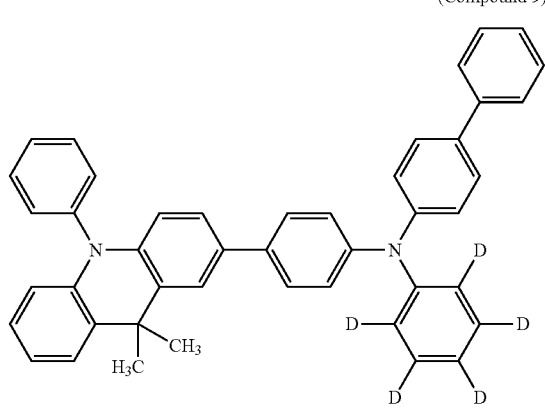
[Chemical Formula 12] (Compound 10)
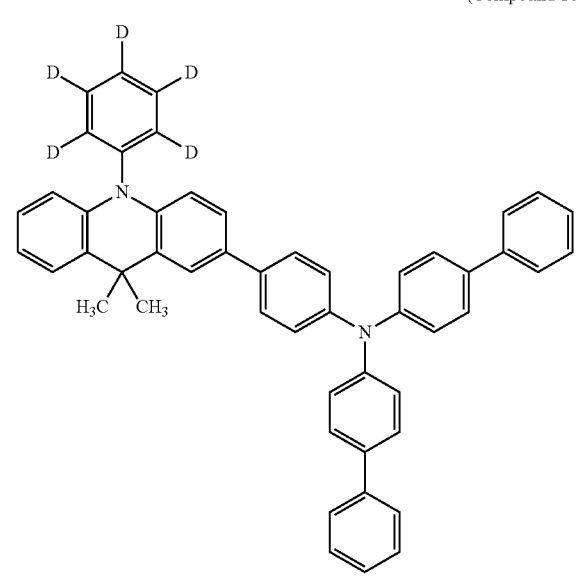
[Chemical Formula 13] (Compound 11)
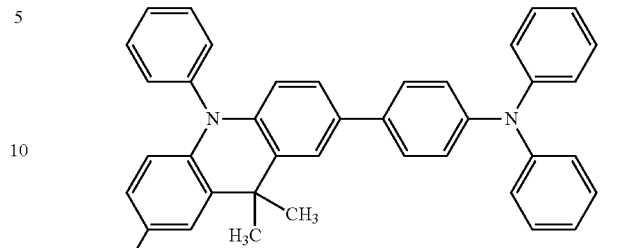
[Chemical Formula 14] (Compound 12)
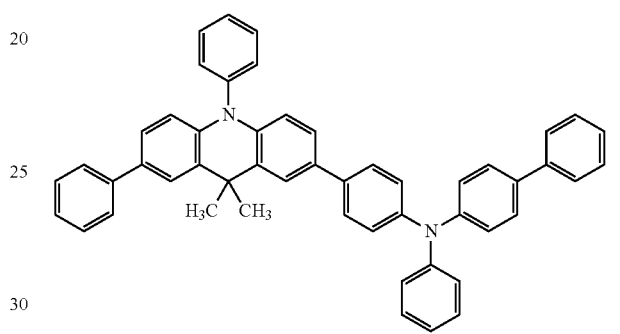
[Chemical Formula 15] (Compound 13)
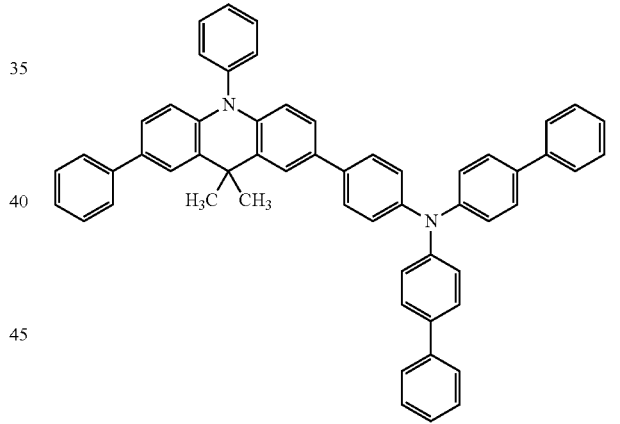
[Chemical Formula 16] (Compound 14)
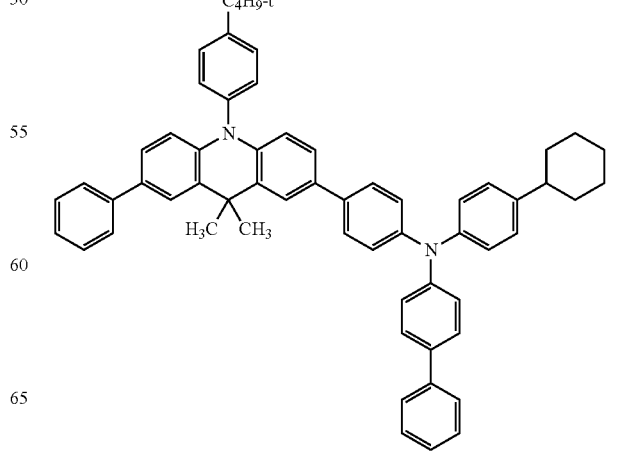

[Chemical Formula 17]
(Compound 15)
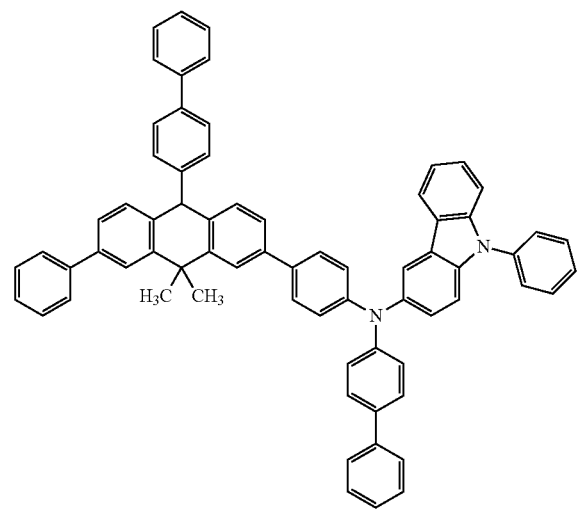
[Chemical Formula 18]
(Compound 16)
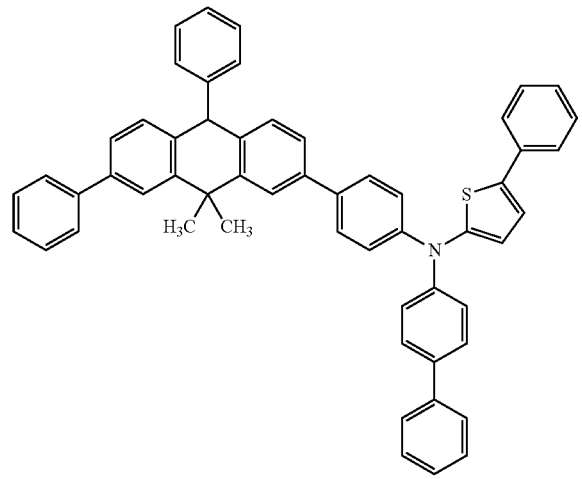
[Chemical Formula 19]
(Compound 17)
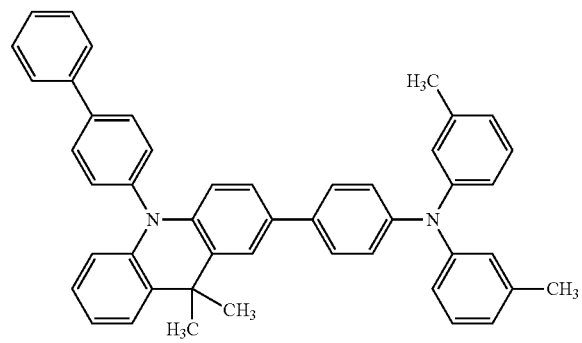
[Chemical Formula 20]
(Compound 18)
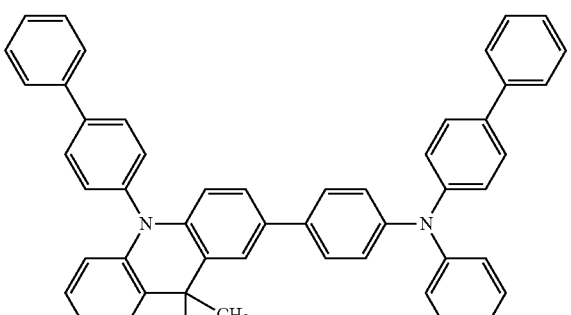
[Chemical Formula 21]
(Compound 19)
[Chemical Formula 22]
(Compound 20)

-continued
[Chemical Formula 23]
(Compound 21)
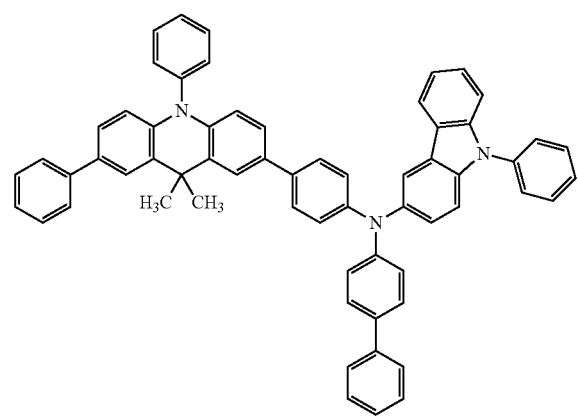
[Chemical Formula 24]
(Compound 22)
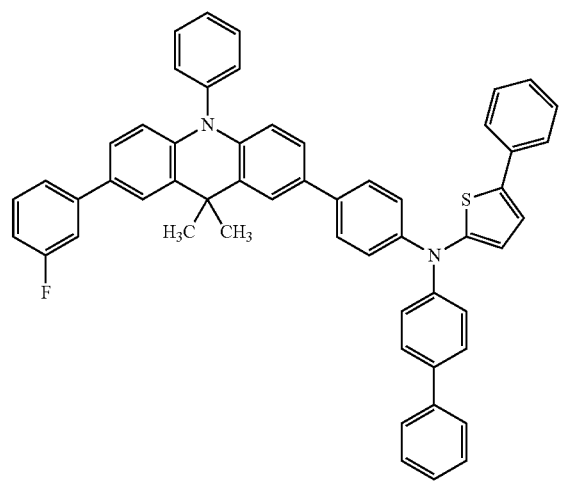
[Chemical Formula 25]
(Compound 23)
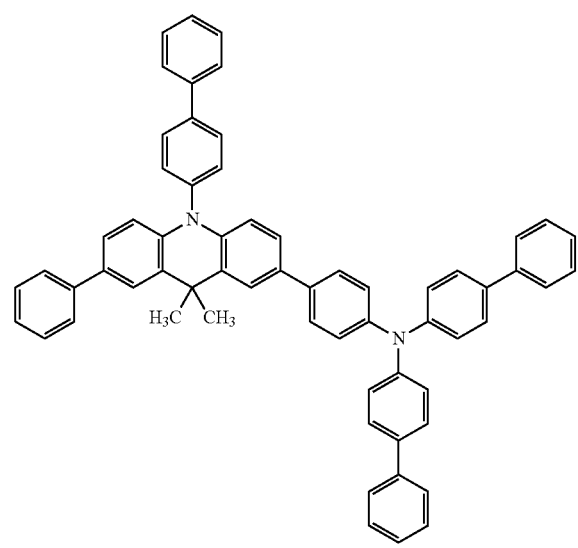
-continued
[Chemical Formula 26]
(Compound 24)
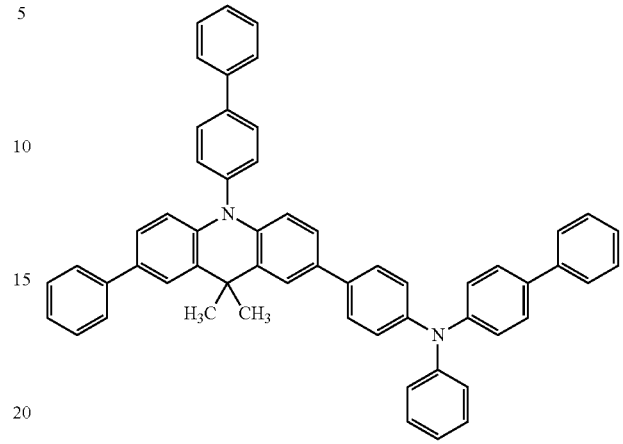
[Chemical Formula 27]
(Compound 25)
[Chemical Formula 28]
(Compound 26)
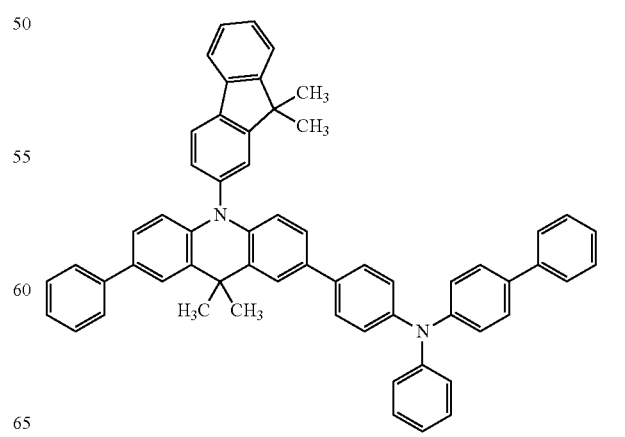

[Chemical Formula 29]
(Compound 27)
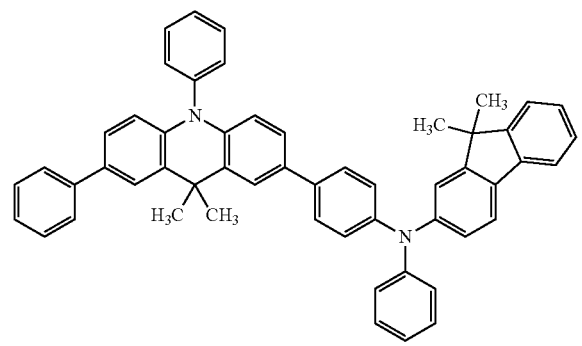
[Chemical Formula 30]
(Compound 28)
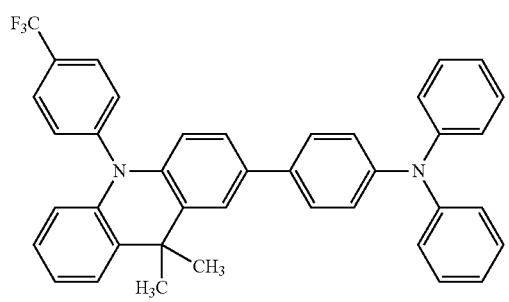
[Chemical Formula 31]
(Compound 29)
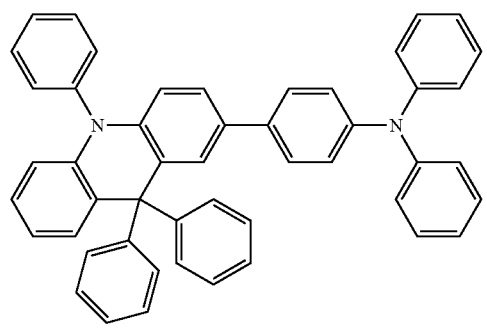
[Chemical Formula 32]
(Compound 30)
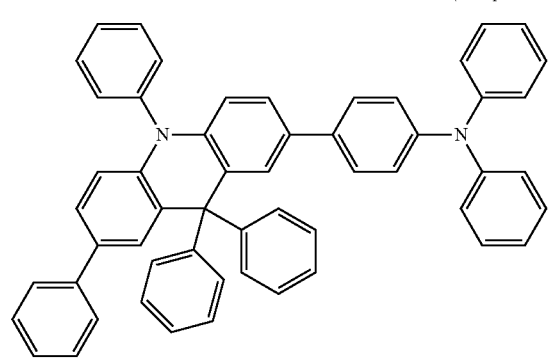
[Chemical Formula 33]
(Compound 31)
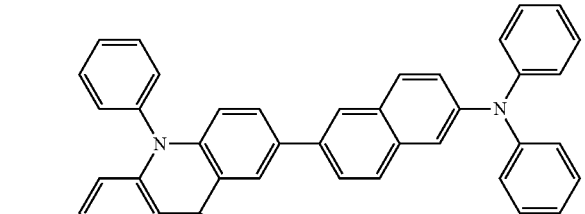
[Chemical Formula 34]
(Compound 32)
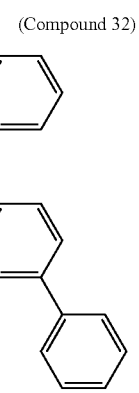
[Chemical Formula 35]
(Compound 33)
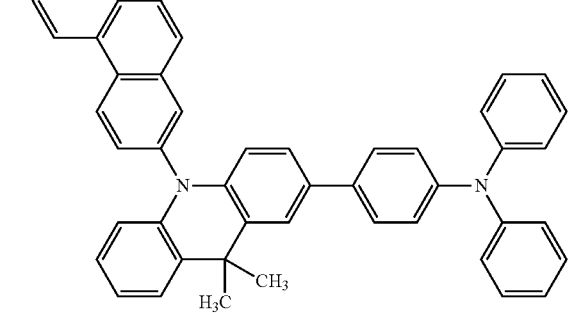
[Chemical Formula 36]
(Compound 34)
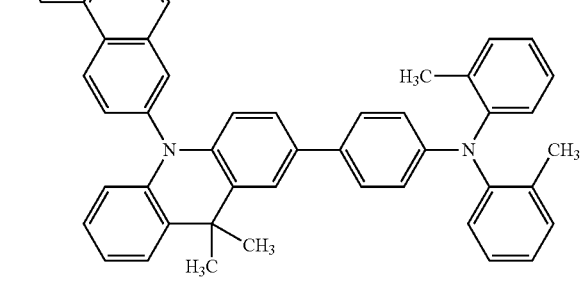

[Chemical Formula 37]
(Compound 35)
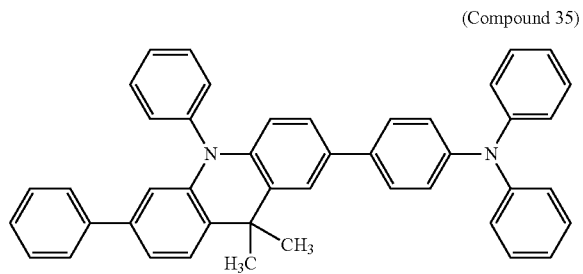
[Chemical Formula 38]
(Compound 36)
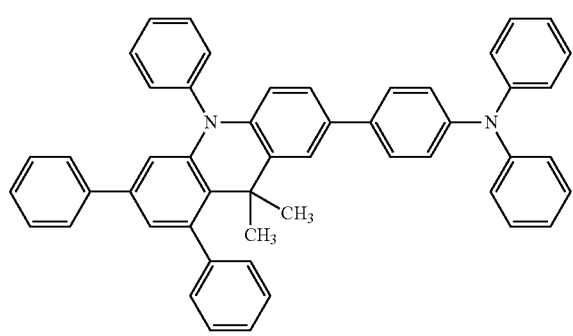
[Chemical Formula 39]
(Compound 37)
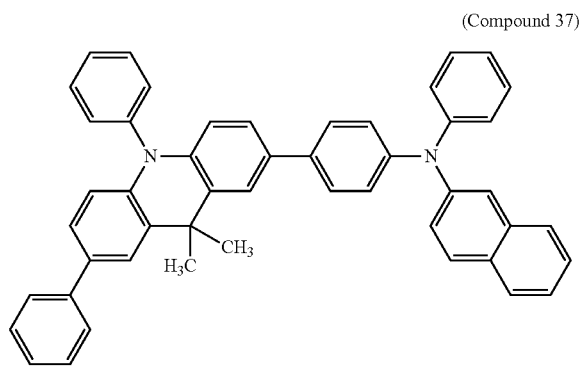
[Chemical Formula 40]
(Compound 38)
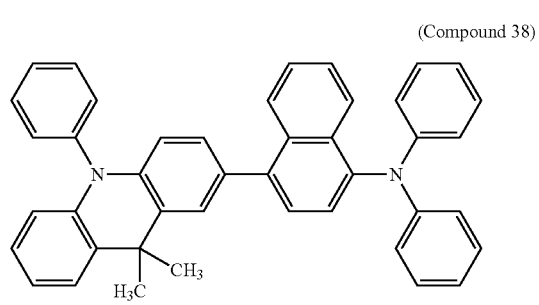
[Chemical Formula 41]
(Compound 39)
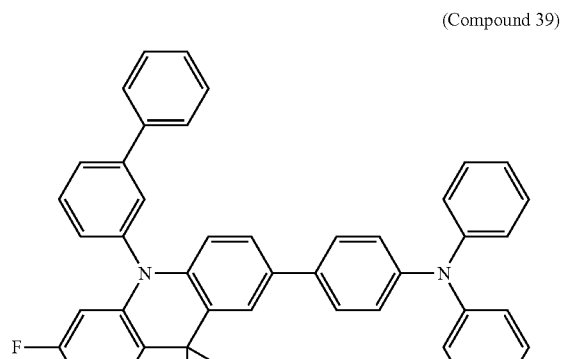
[Chemical Formula 42]
(Compound 40)
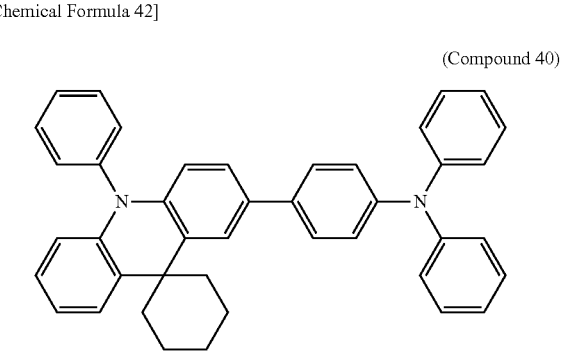
[Chemical Formula 43]
(Compound 41)
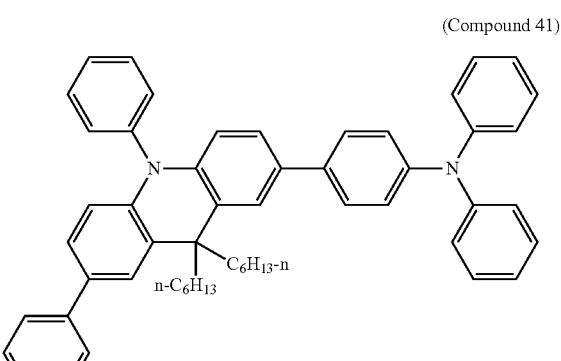
[Chemical Formula 44]
(Compound 42)
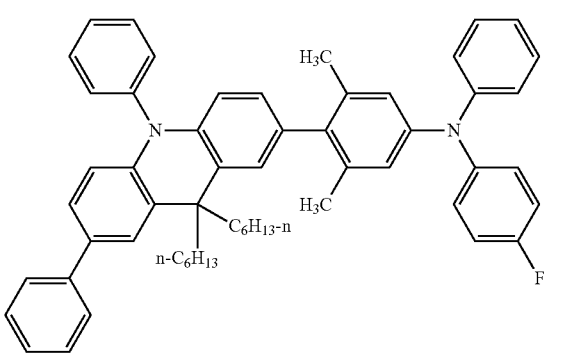

[Chemical Formula 45]
(Compound 43)
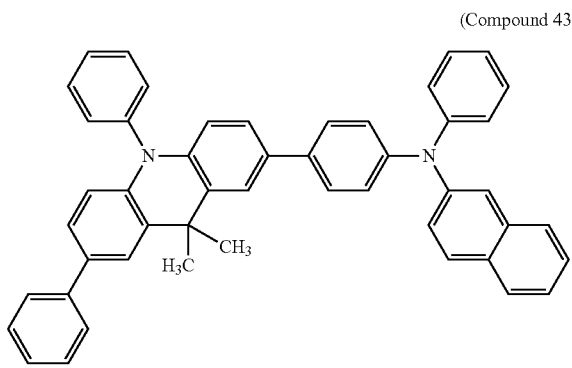
[Chemical Formula 46]
(Compound 44)
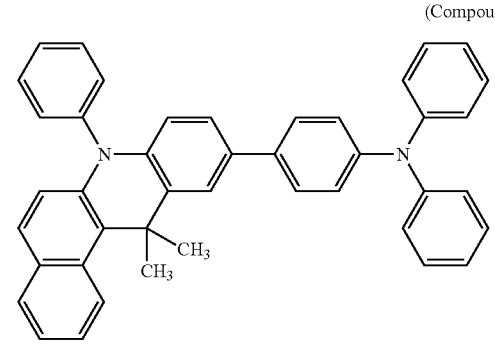
[Chemical Formula 47]
(Compound 45)
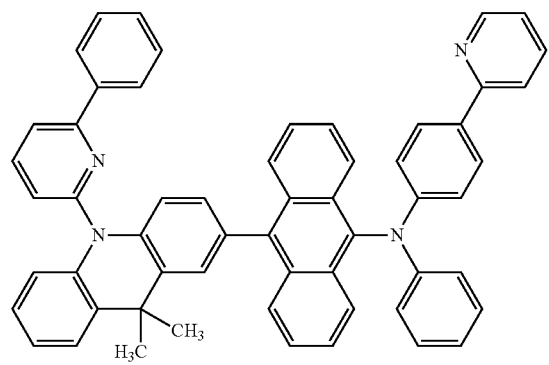
[Chemical Formula 48]
(Compound 46)
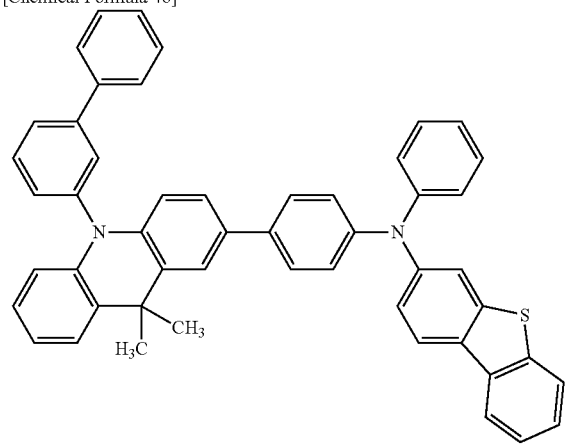
[Chemical Formula 49]
(Compound 47)
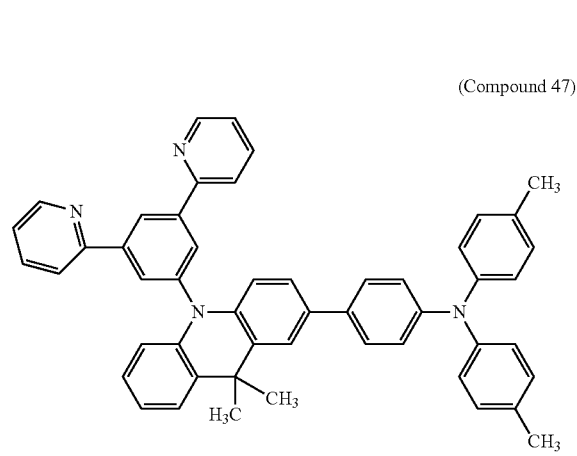
[Chemical Formula 50]
(Compound 48)
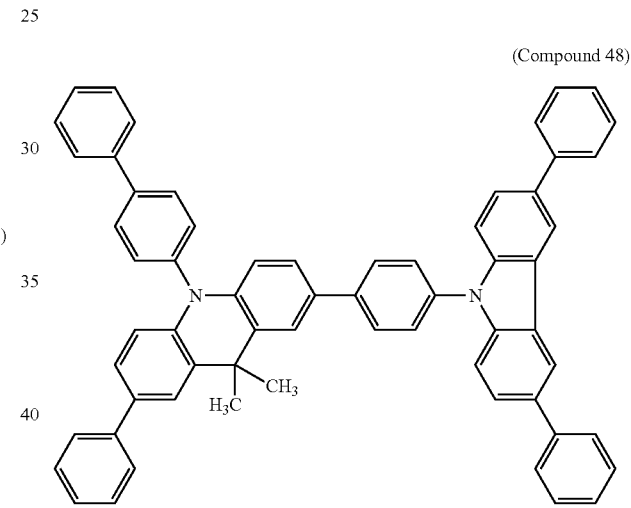
[Chemical Formula 51]
(Compound 49)
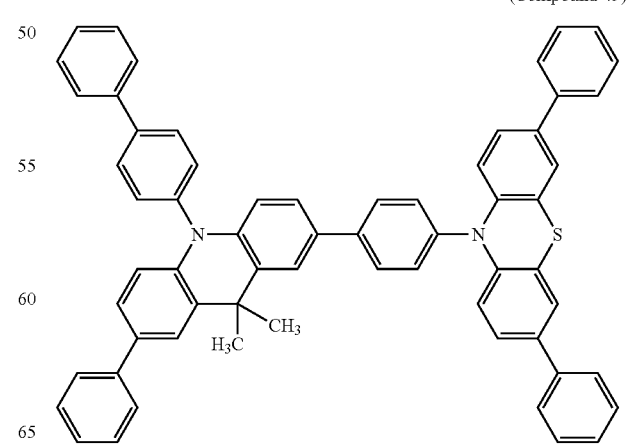

-continued
[Chemical Formula 52]    (Compound 50)
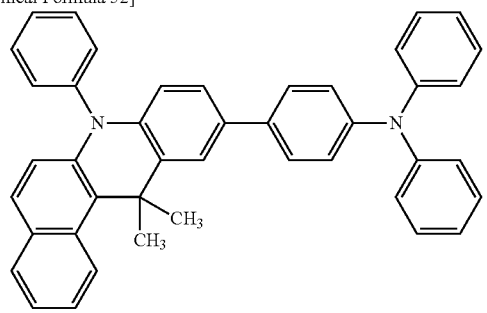
[Chemical Formula 53]    (Compound 51)
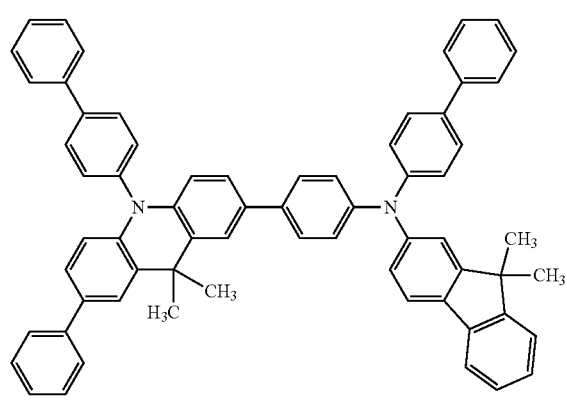
[Chemical Formula 54]    (Compound 52)
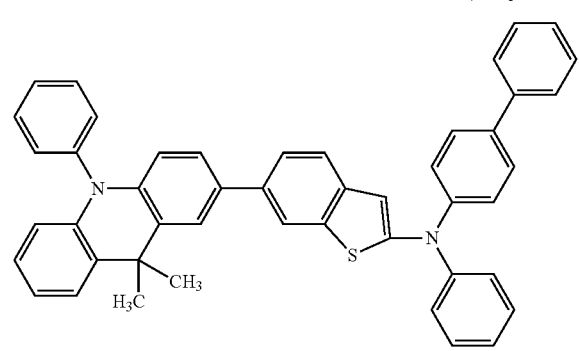
[Chemical Formula 55]    (Compound 53)
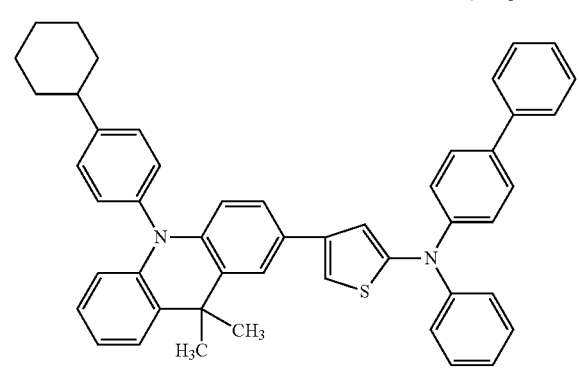
[Chemical Formula 56]    (Compound 54)
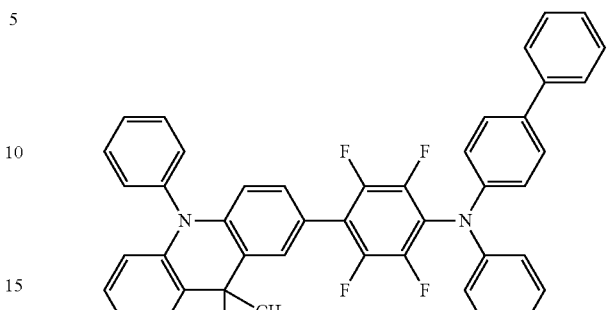
[Chemical Formula 57]    (Compound 55)
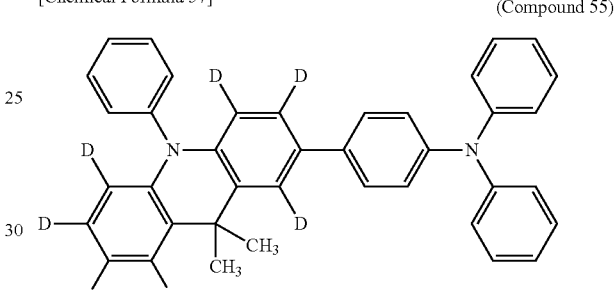
[Chemical Formula 58]    (Compound 56)
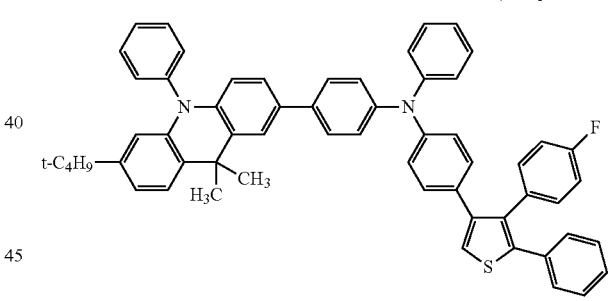
[Chemical Formula 59]    (Compound 57)
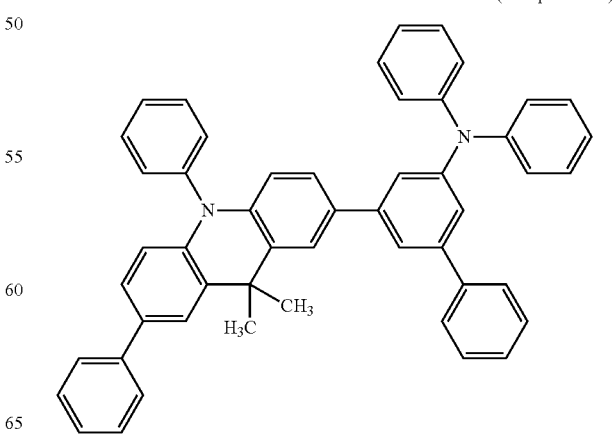

-continued
[Chemcial Formula 60]
(Compound 58)
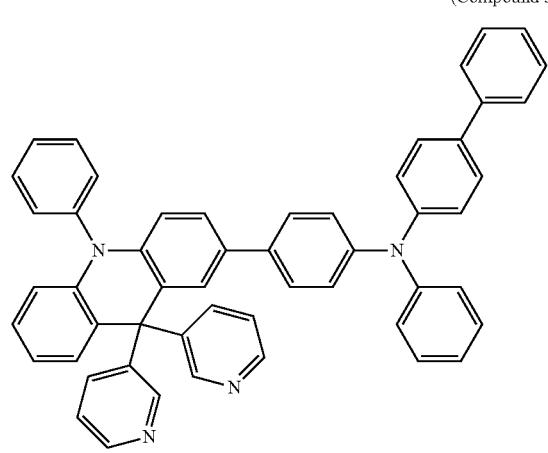
[Chemcial Formula 61]
(Compound 59)
[Chemcial Formula 62]
(Compound 60)
-continued
[Chemical Formula 63]
(Compound 61)
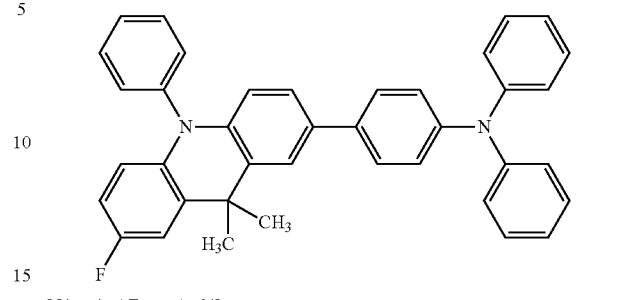
[Chemical Formula 64]
(Compound 62)
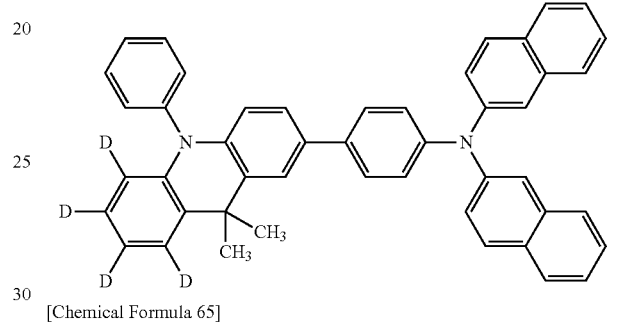
[Chemical Formula 65]
(Compound 63)
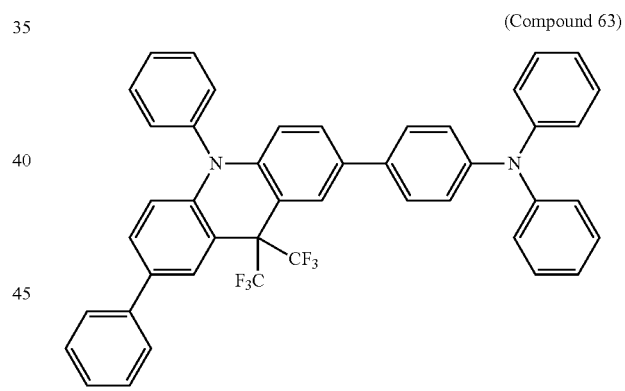
[Chemical Formula 66]
(Compound 64)
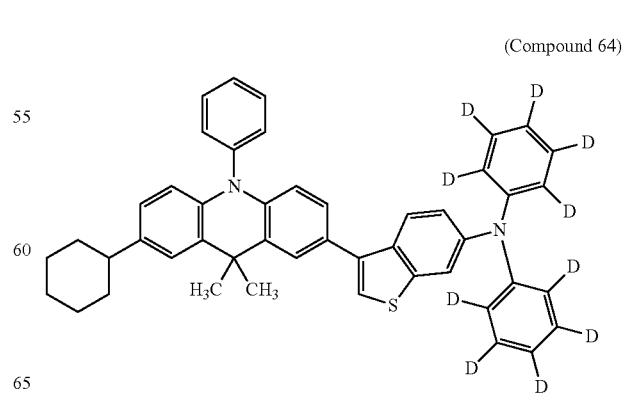

[Chemical Formula 67]
(Compound 65)
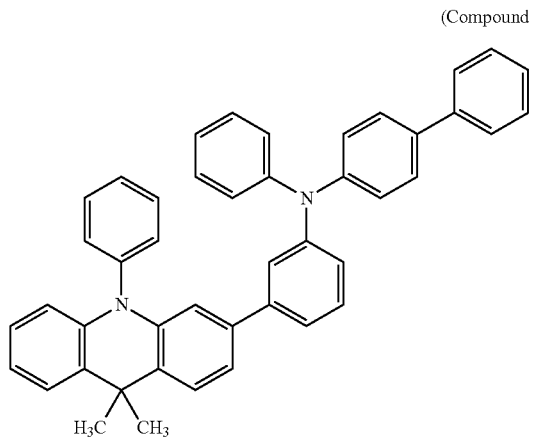
[Chemical Formula 68]
(Compound 66)
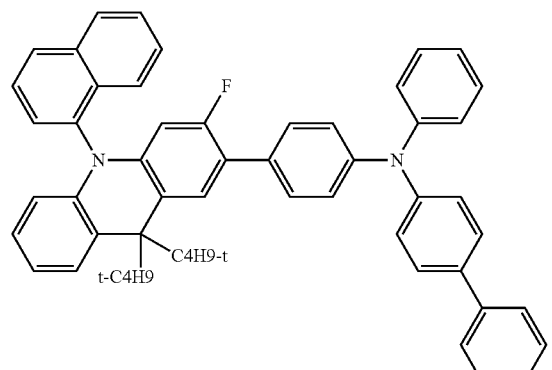
[Chemical Formula 69]
(Compound 67)
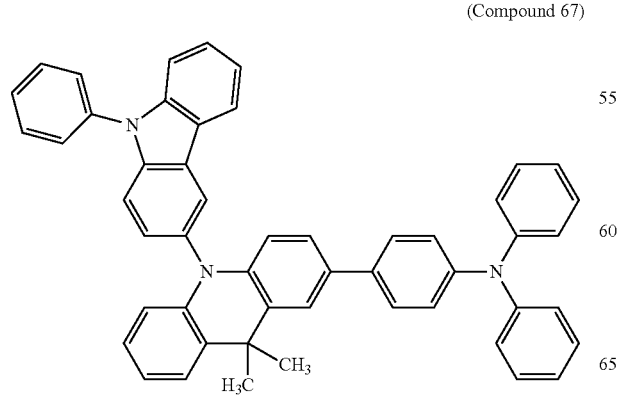
[Chemical Formula 70]
(Compound 68)
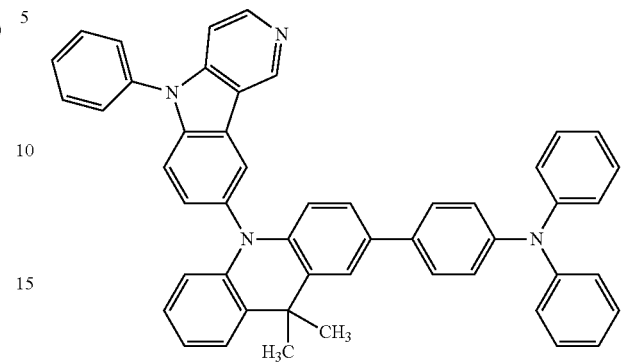
[Chemical Formula 71]
(Compound 69)
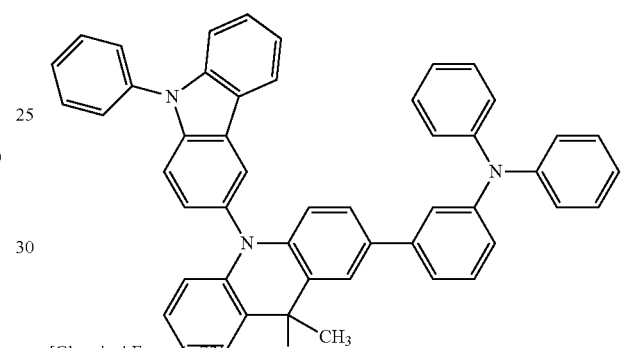
[Chemical Formula 72]
(Compound 70)
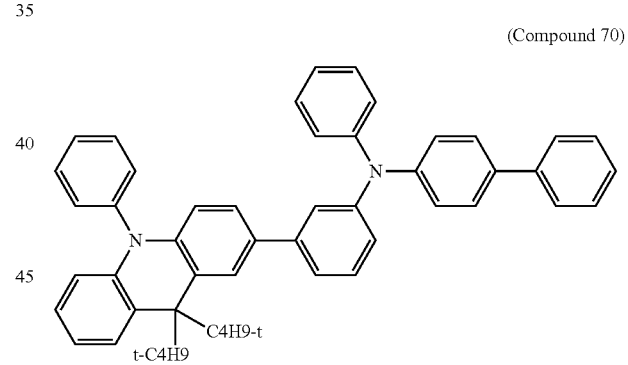
[Chemical Formula 73]
(Compound 71)
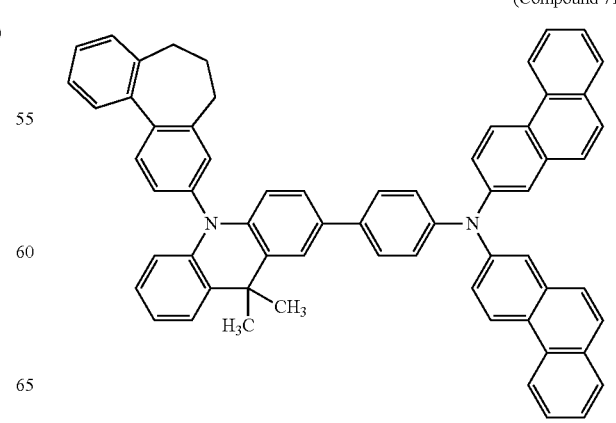

[Chemical Formula 74]

(Compound 72)

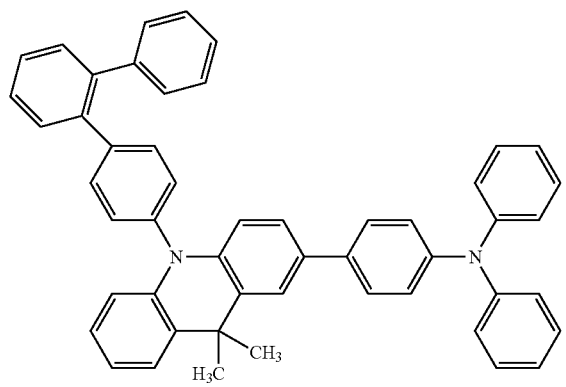

[Chemical Formula 75]

(Compound 73)

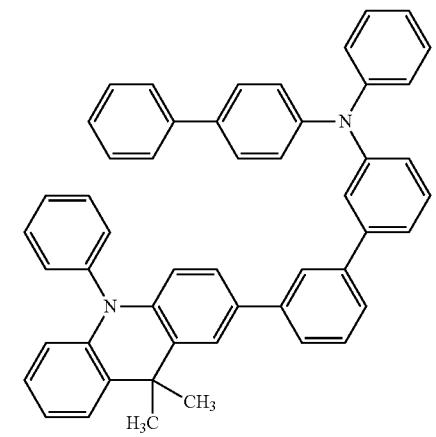

[Chemical Formula 76]

(Compound 74)

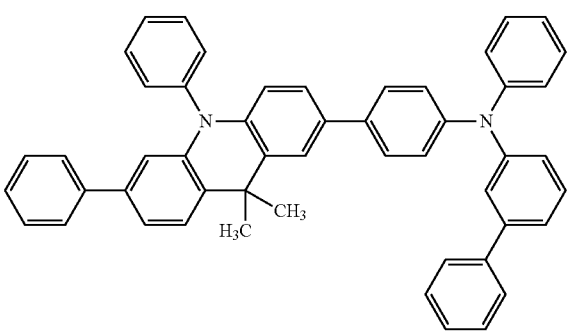

[Chemical Formula 77]

(Compound 75)

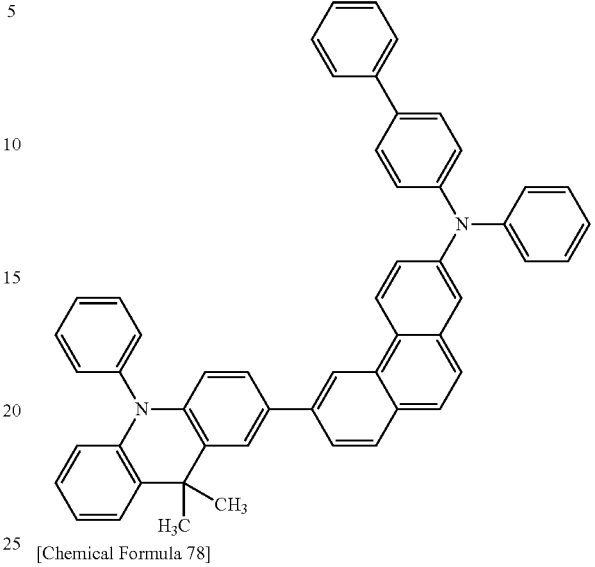

[Chemical Formula 78]

(Compound 76)

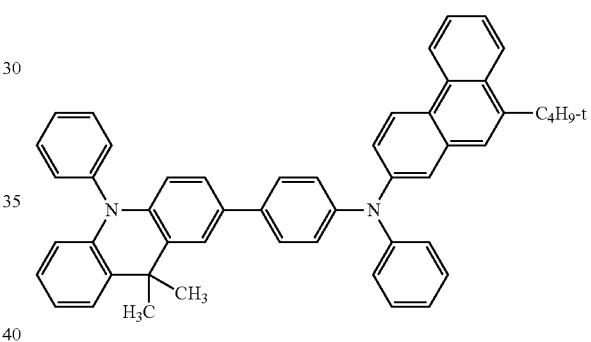

These compounds were purified by methods such as column chromatography, adsorption using, for example, silica gel, activated carbon, or activated clay, and recrystallization or crystallization using a solvent. The compounds were identified by an NMR analysis. A glass transition point (Tg), a melting point, and a work function were measured as material property values. The glass transition point (Tg) can be used as an index of stability in the thin-film state, the melting point as an index of vapor deposition, and the work function as an index of hole transportability.

The glass transition point (Tg) and the melting point were measured by a high-sensitive differential scanning calorimeter (DSC3100S produced by Bruker AXS) using powder.

For the measurement of the work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole transport layer, an electron blocking layer, a light emitting layer, an electron transport layer, and a cathode successively formed on a substrate, optionally with a hole injection layer between the anode and the hole transport layer, or with an electron injection layer between the electron transport layer and the cathode. In such multilayer structures, some of the organic layers may be omitted. For example, the device may be configured to include an anode, a hole transport layer, a light emitting layer, an electron transport layer, and a cathode successively formed on a substrate.

Electrode materials with high work functions such as ITO and gold are used as the anode of the organic EL device of the present invention. The hole injection layer of the organic EL device of the present invention may be made of material such as porphyrin compounds as represented by copper phthalocyanine, starburst-type triphenylamine derivatives, various triphenylamine tetramers, accepting heterocyclic compounds such as hexacyano azatriphenylene, and coating-type polymer materials, in addition to the compounds of general formula (1) having an acridan ring structure of the present invention. These materials may be formed into a thin film by a vapor deposition method or other known methods such as a spin coating method and an inkjet method.

Examples of material used for the hole transport layer of the organic EL device of the present invention can be benzidine derivatives such as N,N'-diphenyl-N,N'-di(m-tolyl)benzidine (hereinafter referred to as TPD), N,N'-diphenyl-N,N'-di($\alpha$-naphthyl)benzidine (hereinafter referred to as NPD), and N,N,N',N'-tetrabiphenylylbenzidine; 1,1-bis[4-(di-4-tolylamino)phenyl]cyclohexane (hereinafter referred to as TAPC); and various triphenylamine trimers and tetramers, in addition to the compounds of general formula (1) having an acridan ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (hereinafter referred to as PEDOT)/poly(styrene sulfonate) (hereinafter referred to as PSS). These materials may be formed into, a thin-film by a vapor deposition method or other known methods such as a spin coating method and an inkjet method.

Further, material used for the hole injection layer or the hole transport layer may be obtained by p-doping trisbromophenylamine hexachloroantimony or the like into the material commonly used for these layers, or may be, for example, polymer compounds each having a TPD structure as a part of the compound structure.

Examples of material used for the electron blocking layer of the organic EL device of the present invention can be compounds having an electron blocking effect, including, for example, carbazole derivatives such as 4,4',4''-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the compounds of general formula (1) having an acridan ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may comprise a host material and a dopant material. Examples of the host material can be thiazole derivatives, benzimidazole derivatives, and polydialkyl fluorene derivatives, in addition to the above light-emitting materials and the compounds of general formula (1) having an acridan ring structure of the present invention. Examples of the dopant material can be quinacridone, coumarin, rubrene, perylene, derivatives thereof, benzopyran derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent light-emitting material. Phosphorescent materials as metal complexes of metals such as iridium and platinum may be used as the phosphorescent light-emitting material. Examples of the phosphorescent materials can be green phosphorescent materials, such as $Ir(ppy)_3$, blue phosphorescent materials such as FIrpic and $FIr_6$, and red phosphorescent materials such as $Btp_2Ir(acac)$. As the hole injecting and transporting host material, the compounds of general formula (1) having an acridan ring structure of the present invention may be used in addition to carbazole derivatives such as 4,4'-di(N-carbazolyl)biphenyl (hereinafter referred to as CBP), TCTA, and mCP. Compounds such as p-bis(triphenylsilyl)benzene (hereinafter referred to as UGH2) and 2,2',2''-(1,3,5-phenylene)-tris(1-phenyl-1H-benzimidazole) (hereinafter referred to as TPBI) may be used as the electron transporting host material to produce a high-performance organic EL device.

In order to avoid concentration quenching, it is preferable to dope the host material with the phosphorescent light-emitting material by co-evaporation in a range of 1 to 30 weight percent to the whole light emitting layer.

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (hereinafter referred to as BCP), and the metal complexes of quinolinol derivatives such as aluminum(III) bis(2-methyl-8-quinolinate)-4-phenylphenolate (hereinafter referred to as BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or laminate of the individually deposited layer and the mixedly deposited layer. These materials may be formed into a thin-film by using a vapor deposition method or other known methods such as a spin coating method and an inkjet method.

Examples of material used for the electron transport layer of the organic EL device of the present invention can be various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to the metal complexes of quinolinol derivatives such as $Alq_3$ and BAlq. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

EXAMPLE 1

Synthesis of [4-(9,9-dimethyl-7,10-diphenylacridan-2-yl)phenyl]-diphenylamine (Compound 11)

2-Bromo-9,9-dimethyl-7,10-diphenylacridan (2.54 g), 4-(diphenylamino)phenylboronic acid (1.75 g), toluene (25 ml), ethanol (2 ml), and a 2M potassium carbonate aqueous solution (9 ml) were added to a reaction vessel in a nitrogen atmosphere and aerated with nitrogen gas for 30 min under ultrasonic irradiation. The mixture was heated after adding tetrakis(triphenylphosphine)palladium (0.20 g) and stirred at 68° C. for 8 hours. The mixture was allowed to cool to a room temperature, and an organic layer was collected by a liquid separating operation. The organic layer was dried with magnesium sulfate and concentrated under reduced pressure to obtain a yellow amorphous crude product. The crude product was recrystallized with n-hexane, dissolved by adding toluene (30 ml), and purified by adsorption using silica gel (1.17 g Methanol (20 ml) was added to this solution to precipitate crystals, and the crystals were further purified by recrystallization using toluene/methanol to obtain a white powder of [4-(9,9-dimethyl-7,10-diphenylacridan-2-yl)phenyl]-diphenylamine (1.9 g; yield 54%).

The structure of the resulting white powder was identified by NMR. The 1H-NMR measurement result is presented in FIG. 1.

1H-NMR (THF-$d_8$) detected 36 hydrogen signals, as follows. δ (ppm)=7.75 (2H), 7.68 (2H), 7.56-7.54 (3H), 7.47 (2H), 7.40 (2H), 7.35 (2H), 7.24-7.18 (7H), 7.09-7.07 (6H), 6.97 (2H), 6.33-6.30 (2H), 1.80 (6H).

EXAMPLE 2

Synthesis of {4-[10-(9,9-dimethyl-9H-fluorene-2-yl)-9,9-dimethylacridan-2-yl]phenyl}-diphenylamine (Compound 19)

[4-(9,9-Dimethylacridan-2-yl)phenyl]-diphenylamine (2.02 g), 2-bromo-9,9-dimethyl-9H-fluorene (1.37 g), a copper powder (0.036 g), potassium carbonate (0.94 g), sodium bisulfite (0.078 g), and dodecane (4 ml) were added to a nitrogen-substituted reaction vessel and stirred at 200° C. for 35 hours. The mixture was allowed to cool to a room temperature, and toluene (30 ml) and methanol (30 ml) were added. Precipitated insoluble matter was removed by filtration and concentrated under reduced pressure to obtain a black crude product. The crude product was purified by column chromatography (carrier: silica gel; eluent: hexane/toluene), crystallized with diisopropyl ether/methanol, and then crystallized with ethyl acetate/diisopropyl ether/hexane to obtain a pale yellowish white powder of {4-[10-(9,9-dimethyl-9H-fluorene-2-yl)-9,9-dimethylacridan-2-yl]phenyl}-diphenylamine (0.96 g; yield 33%).

The structure of the resulting pale yellowish white powder was identified by NMR. The 1H-NMR measurement result is presented in FIG. 2.

1H-NMR (THF-$d_8$) detected 40 hydrogen signals, as follows. δ(ppm)=8.04 (1H), 7.85 (1H), 7.72 (1H), 7.52-7.46 (5H), 7.36-7.30 (3H), 7.23-7.21 (4H), 7.17 (1H), 7.08-7.07 (6H), 6.97 (2H), 6.90-6.87 (2H), 6.38 (1H), 6.34 (1H), 1.73 (6H), 1.53 (6H).

EXAMPLE 3

Synthesis of [4-(9,9-dimethyl-7,10-diphenylacridan-2-yl)phenyl]-(9,9-dimethyl-9H-fluorene-2-yl)-phenylamine (Compound 27)

9,9-Dimethyl-2,10-diphenyl-7-(4,4,5,5-tetramethyl-[1,3,2]dioxaboran-2-yl)acridan (2.02 g), (4-bromophenyl)-(9,9-dimethyl-9H-fluorene-2-yl)-phenylamine (1.90 g), toluene (20 ml), ethanol (2 ml), and a 2M potassium carbonate aqueous solution (6 ml) were added to a nitrogen-substituted reaction vessel and aerated with nitrogen gas for 30 min under ultrasonic irradiation. The mixture was heated after adding tetrakis(triphenylphosphine)palladium (0.14 g) and stirred at 72° C. for 8.5 hours. The mixture was allowed to cool to a room temperature, and an organic layer was collected by a liquid separating operation. The organic layer was dried with magnesium sulfate and concentrated under reduced pressure to obtain a brown crude product. The crude product was purified by column chromatography (carrier: silica gel; eluent: hexane/toluene) and crystallized with acetone/methanol to obtain a white powder of [4-(9,9-dimethyl-7,10-diphenylacridan-2-yl)phenyl]-(9,9-dimethyl-9H-fluorene-2-yl)-phenylamine (1.98 g; yield 64%).

The structure of the resulting white powder was identified by NMR. The 1H-NMR measurement result is presented in FIG. 3.

1H-NMR (THF-$d_8$) detected 44 hydrogen signals, as follows. δ(ppm)=7.76 (2H), 7.68-7.62 (4H), 7.56-7.55 (3H), 7.49 (2H), 7.41-7.35 (5H), 7.29-7.20 (8H), 7.13-7.12 (4H), 7.03 (1H), 6.98 (1H), 6.31 (2H), 1.80 (6H), 1.40 (6H).

EXAMPLE 4

Synthesis of (biphenyl-4-yl)-[4-(9,9-dimethyl-7,10-diphenylacridan-2-yl)phenyl]-phenylamine (Compound 12)

2-Bromo-9,9-dimethyl-7,10-diphenylacridan (3.2 g), (biphenyl-4-yl)-[4-(4,4,5,5-tetramethyl-[1,3,2]dioxaboran-2- yl)phenyl]-phenylamine (3.6 g), toluene (40 ml), ethanol (10 ml), and a 2M potassium carbonate aqueous solution (11 ml) were added to a nitrogen-substituted reaction vessel and aerated with nitrogen gas for 30 min under ultrasonic irradiation. The mixture was heated after adding tetrakis (triphenylphosphine)palladium (0.26 g) and stirred at 72° C. for 7 hours. The mixture was allowed to cool to a room temperature, and methanol (50 ml) was added. A precipitated solid was collected by filtration and washed with water to obtain a red brown crude product. The crude product was dissolved by adding toluene (100 ml) and subjected to adsorptive purification twice using silica gel (3.7 g). The product was then crystallized with toluene/methanol to obtain a white powder of (biphenyl-4-yl)-[4-(9,9-dimethyl-7,10-diphenylacridan-2-yl)phenyl]-phenylamine (3.42 g; yield 68%).

The structure of the resulting white powder was identified by NMR. The 1H-NMR measurement result is presented in FIG. 4.

1H-NMR (THF-$d_8$) detected 40 hydrogen signals, as follows. δ(ppm)=7.77-7.75 (2H), 7.70-7.67 (2H), 7.59-7.50 (9H), 7.41-7.38 (6H), 7.25-7.21 (6H), 7.15-7.13 (6H), 7.00 (1H), 6.33-6.31 (2H), 2.48 (6H).

EXAMPLE 5

Synthesis of bis(biphenyl-4-yl)-[4-(9,9-dimethyl-7,10-diphenylacridan-2-yl)phenyl]amine (Compound 13)

2-Bromo-9,9-dimethyl-7,10-diphenylacridan (2.9 g), bis(biphenyl-4-yl)-[4-(4,4,5,5-tetramethyl-[1,3,2]dioxaboran-2-yl)phenyl]amine (4.0 g), toluene (44 ml), ethanol (11 ml), and a 2M potassium carbonate aqueous solution (8.4 ml) were added to a nitrogen-substituted reaction vessel and aerated with nitrogen gas for 30 min under ultrasonic irradiation. The mixture was heated after adding tetrakis (triphenylphosphine)palladium (0.23 g) and stirred at 72° C. for 4.5 hours. The mixture was allowed to cool to a room temperature, and an organic layer was collected by a liquid separating operation. The organic layer was dried with magnesium sulfate and concentrated under reduced pressure to obtain a red crude product. The crude product was dissolved by adding toluene (75 ml), purified by adsorption using silica gel (5.2 g), and purified by recrystallization using toluene/methanol to obtain a whitish powder of bis(biphenyl-4-yl)-[4-(9,9-dimethyl-7,10-diphenylacridan-2-yl)phenyl]amine (3.19 g; yield 64%).

The structure of the resulting whitish powder was identified by NMR. The 1H-NMR measurement result is presented in FIG. 5.

1H-NMR (THF-$d_8$) detected 44 hydrogen signals, as follows. δ(ppm)=7.77 (2H), 7.69-7.67 (15H), 7.61-7.53 (8H), 7.41-7.18 (11H), 6.33-6.31 (2H), 2.48 (6H).

EXAMPLE 6

Synthesis of (phenyl-4-yl)-[4-{10-(biphenyl-4-yl)-9,9-dimethyl-7-phenylacridan-2-yl}phenyl]-phenylamine (Compound 24)

2-Bromo-10-(biphenyl-4-yl)-9,9-dimethyl-7-phenylacridan (2.7 g), (biphenyl-4-yl)-[4-(4,4,5,5-tetramethyl-[1,3,2]dioxaboran-2-yl)phenyl]-phenylamine (2.8 g), toluene (40 ml), ethanol (10 ml), and a 2M potassium carbonate aqueous solution (8 ml) were added to a nitrogen-substituted reaction vessel and aerated with nitrogen gas for 30 min under ultrasonic irradiation. The mixture was heated after adding tetrakis(triphenylphosphine)palladium (0.13 g) and stirred at 72° C. for 3.5 hours. The mixture was allowed to cool to a room temperature, and methanol (50 ml) was added. A precipitated solid was collected by filtration and washed with water to obtain an orange crude product. The crude product was dissolved by adding toluene (200 ml) and purified by adsorption using silica gel (2.4 g). The product was then crystallized with toluene/methanol to obtain a white powder of (phenyl-4-yl)-[4-{10-(biphenyl-4-yl)-9,9-dimethyl-7-phenylacridan-2-yl}phenyl]-phenylamine (3.07 g; yield 78%).

The structure of the resulting white powder was identified by NMR. The 1H-NMR measurement result is presented in FIG. 6.

1H-NMR (THF-$d_8$) detected 44 hydrogen signals, as follows. δ(ppm)=7.98 (2H), 7.78-7.77 (4H), 7.60-7.39 (12H), 7.37-7.35 (5H), 7.27-7.22 (6H), 7.16-7.13 (6H), 7.01 (1H), 6.42 (2H), 1.82 (6H).

EXAMPLE 7

Synthesis of bis(biphenyl-4-yl)-[4-{10-(biphenyl-4-yl)-9,9-dimethyl-7-phenylacridan-2-yl}phenyl]amine (Compound 23)

2-Bromo-10-(biphenyl-4-yl)-9,9-dimethyl-7-phenylacridan (2.5 g), bis(biphenyl-4-yl)-[4-(4,4,5,5-tetramethyl-[1,3,2]dioxaboran-2-yl)phenyl]amine (3.0 g), toluene (37 ml), ethanol (9.3 ml), and a 2M potassium carbonate aqueous solution (7.2 ml) were added to a nitrogen-substituted reaction vessel and aerated with nitrogen gas for 30 min under ultrasonic irradiation. The mixture was heated after adding tetrakis(triphenylphosphine)palladium (0.11 g) and stirred at 72° C. for 8.5 hours. The mixture was allowed to cool to a room temperature, and methanol (40 ml) was added. A precipitated solid was collected by filtration and washed with water to obtain an orange crude product. The crude product was dissolved by adding toluene (360 ml), purified by adsorption using silica gel (3.6 g), and crystallized with toluene/methanol three times. Further, methanol (60 ml) was added to the product, and the product was washed and purified by heating under reflux to obtain a white powder of bis(biphenyl-4-yl)-[4-{10-(biphenyl-4-yl)-9,9-dimethyl-7-phenylacridan-2-yl}phenyl]amine (3.04 g; yield 75%).

The structure of the resulting white powder was identified by NMR. The 1H-NMR Measurement result is presented in FIG. 7.

1H-NMR (THF-$d_8$) detected 48 hydrogen signals, as follows. δ(ppm)=7.99 (2H), 7.79-7.77 (4H), 7.60-7.48 (16H), 7.40-7.35 (7H), 7.28-7.19 (11H), 6.42 (2H), 1.82 (6H).

EXAMPLE 8

The melting point and glass transition point of the compounds of the present invention were determined using a high-sensitive differential scanning calorimeter (DSC 3100S produced by Bruker AXS).

|  | Melting point | Glass transition point |
|---|---|---|
| Compound of Example 1 of the present invention | 248° C. | 106° C. |

-continued

|  | Melting point | Glass transition point |
|---|---|---|
| Compound of Example 2 of the present invention | 142° C. | 115° C. |
| Compound of Example 3 of the present invention | 162° C. | 129° C. |
| Compound of Example 4 of the present invention | 254° C. | 118° C. |
| Compound of Example 5 of the present invention | 258° C. | 136° C. |
| Compound of Example 6 of the present invention | 164° C. | 130° C. |

The compounds of the present invention have glass transition points of 100° C. or higher, demonstrating that the compounds of the present invention have a stable thin-film state.

EXAMPLE 9

A 100 nm-thick vapor-deposited film was fabricated on an ITO substrate using the compounds of the present invention, and a work function was measured using an atmosphere photoelectron spectrometer (Model AC-3 produced by Riken Keiki Co., Ltd.).

|  | Work function |
|---|---|
| Compound of Example 1 of the present invention | 5.45 eV |
| Compound of Example 2 of the present invention | 5.41 eV |
| Compound of Example 3 of the present invention | 5.45 eV |
| Compound of Example 4 of the present invention | 5.41 eV |
| Compound of Example 5 of the present invention | 5.41 eV |
| Compound of Example 6 of the present invention | 5.49 eV |

As the results show, the compounds of the present invention have desirable energy levels compared to the work function 5.4 eV of common hole transport materials such as NPD and TPD, and thus possess desirable hole transportability.

EXAMPLE 10

An organic EL device, as illustrated in FIG. 8, was fabricated by forming a hole injection layer 3, a hole transport layer 4, a light emitting layer 5, an electron transport layer 6, an electron injection layer 7, and a cathode (an aluminum electrode) 8 in this order by vapor deposition on a glass substrate 1 that had been provided beforehand with an ITO electrode as a transparent anode 2.

Specifically, the glass substrate 1 with ITO formed with a film thickness of 150 nm thereon was washed with an organic solvent and subjected to an oxygen plasma treatment to wash the surface. The glass substrate with the ITO electrode was then installed in a vacuum vapor deposition apparatus, and the pressure was reduced to 0.001 Pa or less. This was followed by the formation of the hole injection layer 3 by forming Compound 77 of the structural formula below over the transparent anode 2 in a film thickness of 20 nm. The hole transport layer 4 was then formed on the hole injection layer 3 by forming the compound of Example 2 of the present invention (Compound 19) in a film thickness of 40 nm. Thereafter, the light emitting layer 5 was formed on the hole transport layer 4 by forming Compounds 78 and 79 of the structural formulae below in a film thickness of 30 nm using dual vapor deposition at a deposition rate ratio of Compound 78:Compound 79=5:95. Then, the electron transport layer 6 was formed on the light emitting layer 5 by forming Alq$_3$ in a film thickness of 30 nm. The electron injection layer 7 was then formed on the electron transport layer 6 by forming lithium fluoride in a film thickness of 0.5 nm. Finally, the cathode 8 was formed by vapor-depositing aluminum in a film thickness of 150 nm. The characteristics of the organic EL device thus fabricated were measured in the atmosphere at an ordinary temperature.

Table 1 summarizes the results of the emission characteristics measurements performed by applying a DC voltage to the organic EL device produced by using the compound of Example 2 of the present invention (Compound 19).

[Chemical Formula 79]

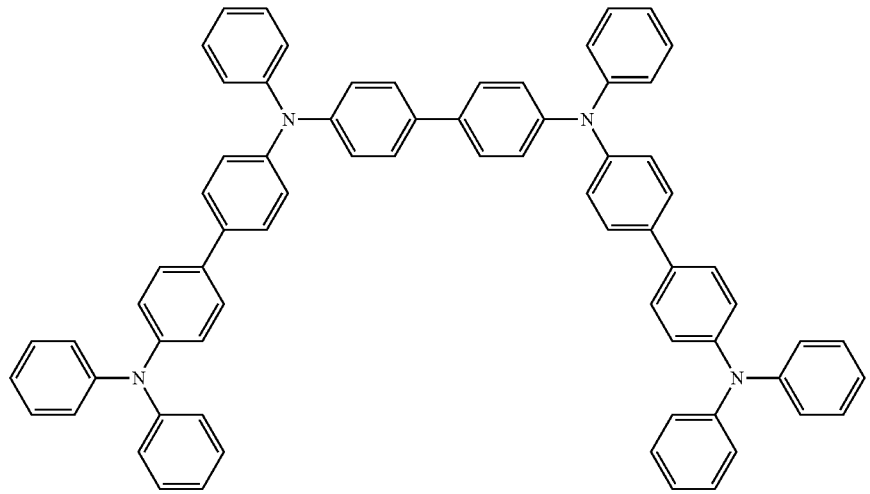

(Compound 77)

[Chemical Formula 80]

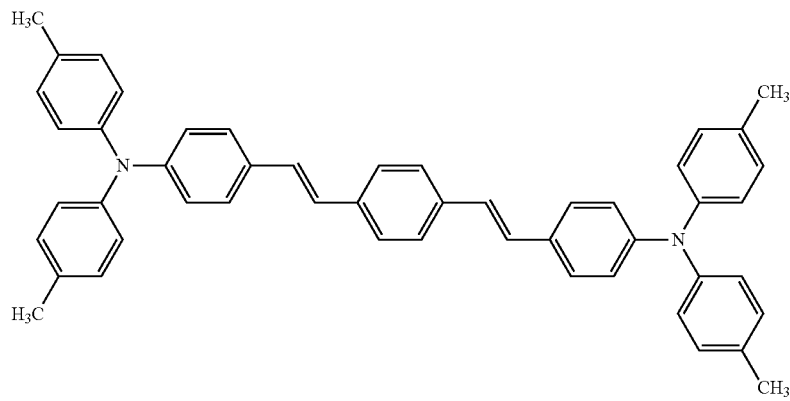
(Compound 78)

[Chemical Formula 81]

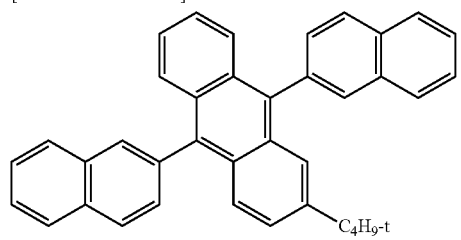
(Compound 79)

EXAMPLE 11

An organic EL device was fabricated under the same conditions used in Example 10, except that the compound of Example 5 of the present invention (Compound 13) was formed in a film thickness of 40 nm as the material of the hole transport layer 4, instead of using the compound of Example 2 of the present invention (Compound 19). The characteristics of the organic EL device thus fabricated were measured in the atmosphere at an ordinary temperature. Table 1 summarizes the results of the emission characteristics measurements performed by applying a DC voltage to the organic EL device.

COMPARATIVE EXAMPLE 1

For comparison, an organic EL device was fabricated under the same conditions used in Example 10, except that Compound 80 of the structural formula below was formed in a film thickness of 40 nm as the material of the hole transport layer 4, instead of using the compound of Example 2 of the present invention (Compound 19). The characteristics of the organic EL device thus fabricated were measured in the atmosphere at an ordinary temperature. Table 1 summarizes the results of the emission characteristics measurements performed by applying a DC voltage to the organic EL device.

[Chemical Formula 82]

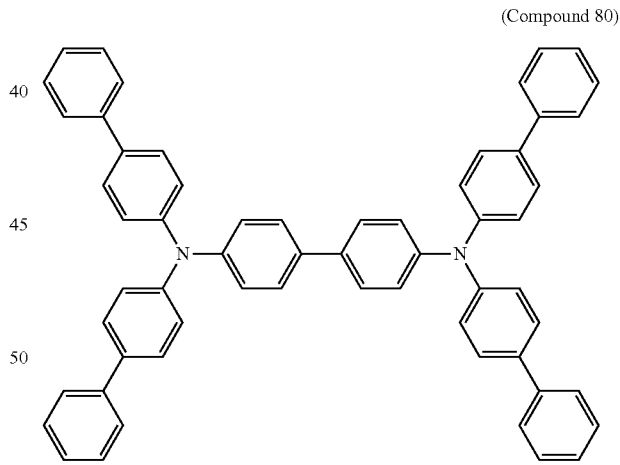
(Compound 80)

TABLE 1

|  |  | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) |
| --- | --- | --- | --- | --- | --- |
| Ex. 10 | Compound 19 | 4.82 | 960 | 9.61 | 6.26 |
| Ex. 11 | Compound 13 | 4.96 | 910 | 9.10 | 5.76 |
| Com. Ex. 1 | Compound 80 | 5.17 | 902 | 9.03 | 5.49 |

As shown in Table 1, the driving voltage when applying a current with a current density of 10 mA/cm² was 4.82 V for the compound of Example 2 of the present invention (Compound 19) and 4.96 V for the compound of Example 5 of the present invention (Compound 13), both of which were lower than 5.17 V of Compound 80. The power efficiencies of the compound of Example 2 in the present invention (Compound 19) and the compound of Example 5 in the present invention (Compound 13) were 6.26 lm/W and 5.76 lm/W respectively, which showed improvement over the power efficiency 5.49 lm/W of Compound 80. Further, the compounds of the present invention were improved in both of the luminance and the luminous efficiency compared to Compound 80.

As the above results clearly demonstrate, the organic EL devices using the compounds having an acridan ring structure in the present invention has achieved improvements in luminous efficiency and power efficiency, and a lower actual driving voltage compared to the organic EL device using the Compound 80.

INDUSTRIAL APPLICABILITY

The compounds having an acridan ring structure of the present invention have high hole transportability, excel in amorphousness, and have a stable thin-film state. The compounds are therefore excellent as the compounds for organic EL devices. The organic EL devices fabricated with the compounds can have high luminous efficiency and high power efficiency and can have a low actual driving voltage to improve durability. There are potential applications for, for example, home electric appliances and illuminations.

DESCRIPTION OF REFERENCE NUMERAL

1 Glass substrate
2 Transparent electrode
3 Hole injection layer
4 Hole transport layer
5 Light emitting layer
6 Electron transport layer
7 Electron injection layer
8 Cathode

The invention claimed is:

1. A compound of the following general formula (2) having an acridan ring structure,

[Chemical Formula 2]

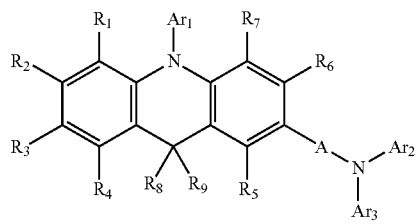

(2)

wherein A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics; $Ar_1$ is substituted or unsubstituted phenyl or substituted or unsubstituted biphenyl, $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_3$ represents a substituted or unsubstituted phenyl group; $R_1$, $R_2$ and $R_4$ are hydrogen; $R_5$ $R_6$ and $R_7$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_8$ and $R_9$ represent methyl.

2. A compound of the following general formula (3) having an acridan ring structure,

[Chemical Formula 3]

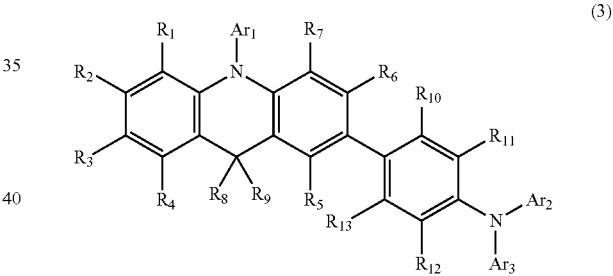

(3)

wherein $Ar_1$ is substituted or unsubstituted phenyl or substituted or unsubstituted biphenyl, $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_3$ represents a substituted or unsubstituted phenyl group; $R_1$, $R_2$ and $R_4$ are hydrogen; $R_5$ $R_6$, $R_7$ and $R_{10}$ to $R_{13}$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a sub stituent, linear or branched alkyloxy of 1 to 6carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_1$ and $R_2$, $R_2$ and $R_3$, $R_3$ and $R_4$, $R_6$ and $R_7$, $R_{10}$ and $R_{11}$, and $R_{12}$ and $R_{13}$ may bind to each other via a single bond, substituted or unsubstituted methylene, an oxygen atom, or a sulfur atom to form a ring; and $R_8$ and $R_9$ represent methyl.

3. A compound of the following general formula (4) having an acridan ring structure,

[Chemical Formula 4]

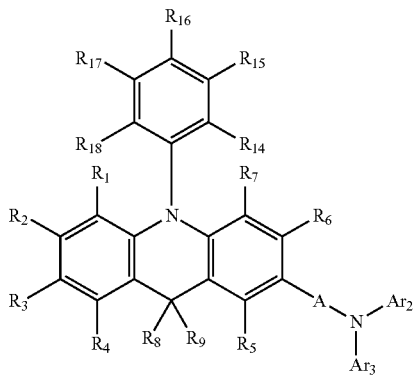

(4)

wherein A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics; $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_3$ represents a substituted or unsubstituted phenyl group; $R_1$, $R_2$ and $R_4$ are hydrogen; $R_5$ $R_6$, $R_7$ and $R_{14}$ to $R_{18}$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_1$ and $R_2$, $R_2$ and $R_3$, $R_3$ and $R_4$, $R_6$ and $R_7$, $R_{14}$ and $R_{15}$, and $R_{15}$ and $R_{16}$, $R_{16}$ and $R_{17}$, and $R_{17}$ and $R_{18}$ may bind to each other via a single bond, substituted or unsubstituted methylene, an oxygen atom, or a sulfur atom to form a ring; and $R_8$ and $R_9$ represent methyl.

4. The compound having an acridan ring structure according to claim 2, wherein the compound is represented by the following general formula (4'),

[Chemical Formula 4']

[Chemical Formula 5]

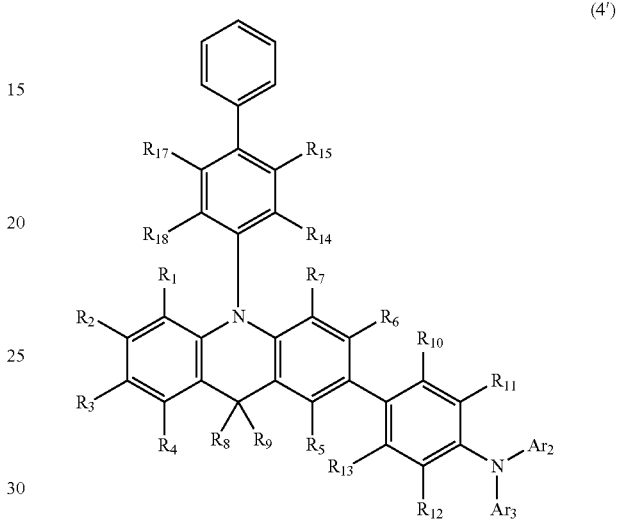

(4')

wherein $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_3$ represents a substituted or unsubstituted phenyl group; $R_1$, $R_2$ and $R_4$ are hydrogen; $R_5$ $R_6$, $R_7$, $R_{10}$ to $R_{13}$, $R_{14}$, $R_{15}$, $R_{17}$, and $R_{18}$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_1$ and $R_2$, $R_2$ and $R_3$, $R_3$ and $R_4$, $R_6$ and $R_7$, $R_{10}$ and $R_{11}$, $R_{12}$ and $R_{13}$, $R_{14}$ and $R_{15}$, and $R_{17}$ and $R_{18}$ may bind to each other via a single bond, substituted or unsubstituted methylene, an oxygen atom, or a sulfur atom to form a ring; and $R_8$ and $R_9$ represent methyl.

5. The compound having an acridan ring structure according to claim 3, wherein the compound is represented by the following general formula (4'''),

[Chemical Formula 7]

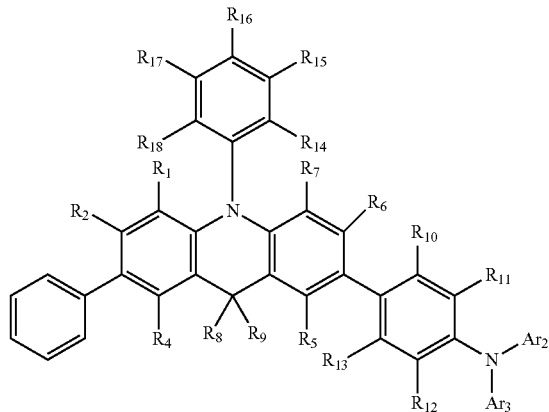

(4''')

wherein $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_1$, $R_2$ and $R_4$ are hydrogen; $R_5$ to $R_7$, $R_{10}$ to $R_{13}$, and $R_{14}$ to $R_{18}$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_1$ and $R_2$, $R_6$ and $R_7$, $R_{10}$ and $R_{11}$, $R_{12}$ and $R_{13}$, $R_{14}$ and $R_{15}$, $R_{15}$ and $R_{16}$, $R_{16}$ and $R_{17}$, and $R_{17}$ and $R_{18}$ may bind to each other via a single bond, substituted or unsubstituted methylene, an oxygen atom, or a sulfur atom to form a ring; and $R_8$ and $R_9$ represent methyl.

6. The compound having an acridan ring structure according to claim 3, wherein the compound is represented by the following general formula (4''''),

[Chemical Formula 4'''']

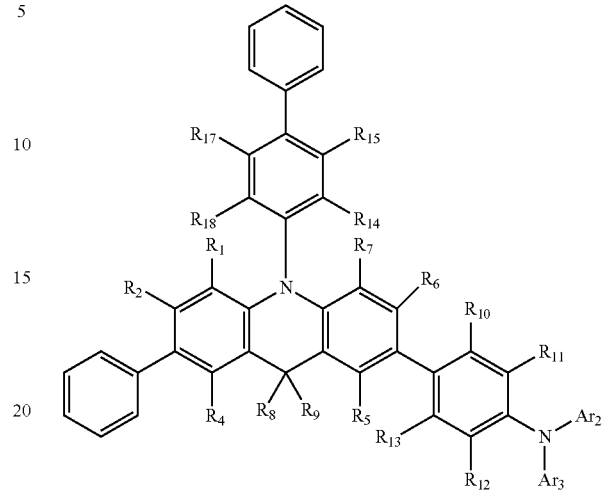

(4'''')

wherein $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_2$ and $Ar_3$ may directly bind to each other via a single bond or via substituted or unsubstituted methylene, an oxygen atom, or a sulfur atom to form a ring, and substituents of $Ar_2$ and $Ar_3$ may bind to each other via a single bond, substituted or unsubstituted methylene, an oxygen atom, or a sulfur atom to form a ring; $R_1$, $R_2$ and $R_4$ are hydrogen; $R_5$ to $R_7$, $R_{10}$ to $R_{13}$, $R_{14}$, $R_{15}$, $R_{17}$, and $R_{18}$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_1$ and $R_2$, $R_6$ and $R_7$, $R_{10}$ and $R_{11}$, $R_{12}$ and $R_{13}$, $R_{14}$ and $R_{15}$, and $R_{17}$ and $R_{18}$ may bind to each other via a single bond, substituted or unsubstituted methylene, an oxygen atom, or a sulfur atom to form a ring; and $R_8$ and $R_9$ represent methyl.

7. An organic electroluminescent device that comprises a pair of electrodes, and one or more organic layers sandwiched between the pair of electrodes,
wherein the compound having an acridan ring structure of claim 1 is used as a constituent material of at least one organic layer.

8. The organic electroluminescent device according to claim 7, wherein the organic layer is a hole transport layer.

9. The organic electroluminescent device according to claim 7, wherein the organic layer is an electron blocking layer.

10. The organic electroluminescent device according to claim 7, wherein the organic layer is a hole injection layer.

11. The organic electroluminescent device according to claim 7, wherein the organic layer is a light emitting layer.

12. An organic electroluminescent device that comprises a pair of electrodes, and one or more organic layers sandwiched between the pair of electrodes,
   wherein the compound having an acridan ring structure of claim 2 is used as a constituent material of at least one organic layer.

13. An organic electroluminescent device that comprises a pair of electrodes, and one or more organic layers sandwiched between the pair of electrodes,
   wherein the compound having an acridan ring structure of claim 3 is used as a constituent material of at least one organic layer.

14. An organic electroluminescent device that comprises a pair of electrodes, and one or more organic layers sandwiched between the pair of electrodes,
   wherein the compound having an acridan ring structure of claim 4 is used as a constituent material of at least one organic layer.

15. An organic electroluminescent device that comprises a pair of electrodes, and one or more organic layers sandwiched between the pair of electrodes,
   wherein the compound having an acridan ring structure of claim 5 is used as a constituent material of at least one organic layer.

16. An organic electroluminescent device that comprises a pair of electrodes, and one or more organic layers sandwiched between the pair of electrodes,
   wherein the compound having an acridan ring structure of claim 6 is used as a constituent material of at least one organic layer.

* * * * *